(12) United States Patent
Kurobe et al.

(10) Patent No.: US 12,239,303 B2
(45) Date of Patent: Mar. 4, 2025

(54) MEDICAL MATERIAL

(71) Applicant: GUNZE LIMITED, Ayabe (JP)

(72) Inventors: Hirotsugu Kurobe, Niihama (JP); Saki Okumura, Ayabe (JP); Yuuki Kato, Ayabe (JP); Koji Yamauchi, Ayabe (JP)

(73) Assignee: GUNZE LIMITED, Ayabe (JP)

( * ) Notice: Subject to any disclaimer, the term of this patent is extended or adjusted under 35 U.S.C. 154(b) by 424 days.

(21) Appl. No.: 17/610,921

(22) PCT Filed: Jul. 7, 2020

(86) PCT No.: PCT/JP2020/026561
§ 371 (c)(1),
(2) Date: Nov. 12, 2021

(87) PCT Pub. No.: WO2021/010229
PCT Pub. Date: Jan. 21, 2021

(65) Prior Publication Data
US 2022/0218321 A1   Jul. 14, 2022

(30) Foreign Application Priority Data

Jul. 18, 2019   (JP) .................................. 2019-132833
Oct. 1, 2019   (JP) .................................. 2019-181505

(51) Int. Cl.
*A61B 17/00*   (2006.01)

(52) U.S. Cl.
CPC .............................. *A61B 17/0057* (2013.01); *A61B 2017/00004* (2013.01); *A61B 2017/00597* (2013.01);
(Continued)

(58) Field of Classification Search
CPC ........... A61B 2017/00004; A61B 2017/00597; A61B 2017/00606; A61B 2017/00623
See application file for complete search history.

(56) References Cited

U.S. PATENT DOCUMENTS 3,874,388 A * 4/1975 King .................. A61B 17/0057
606/232
2005/0038470 A1* 2/2005 van der Burg ... A61B 17/12172
606/213
(Continued)

FOREIGN PATENT DOCUMENTS

JP   2008-512139 A   4/2008
JP   2018-514358 A   6/2018
(Continued)

OTHER PUBLICATIONS

International Search Report, issued in PCT/JP2020/026561, dated Oct. 6, 2020.

*Primary Examiner* — Alexander J Orkin
(74) *Attorney, Agent, or Firm* — Birch, Stewart, Kolasch & Birch, LLP

(57) ABSTRACT

A hole closing material achieves less invasive treatment for atrial septal defect with no or little possibility of problems in the late post-treatment period. The hole closing material includes two tubular bodies (first tubular portion and second tubular portion) having a mesh structure formed of a bioabsorbable linear material, and includes: a proximal connecting part connected to a first end; and a distal connecting part connected to a second end and screwed to a delivery cable. The proximal connecting part and the distal connecting part are capable of selectively achieving: "locked" in which the proximal connecting part and the distal connecting part remain united; and "unlocked" in which the proximal connecting part and the distal connecting part do not remain united. The delivery cable passes through the substantially middle portion, is inserted into a hollow tube of the proximal connecting part, and passes out of the hole closing material in a direction from the second end to the first end.

7 Claims, 37 Drawing Sheets

(52) U.S. Cl.
CPC ............... *A61B 2017/00601* (2013.01); *A61B 2017/00606* (2013.01); *A61B 2017/00623* (2013.01)

(56) References Cited

U.S. PATENT DOCUMENTS

| | | | | |
|---|---|---|---|---|
| 2005/0273135 | A1* | 12/2005 | Chanduszko | A61B 17/0057 606/213 |
| 2006/0009800 | A1 | 1/2006 | Christianson et al. | |
| 2006/0265004 | A1* | 11/2006 | Callaghan | A61B 17/50 606/213 |
| 2007/0073337 | A1* | 3/2007 | Abbott | A61B 17/0057 606/213 |
| 2007/0112381 | A1* | 5/2007 | Figulla | A61B 17/0057 606/213 |
| 2007/0167981 | A1* | 7/2007 | Opolski | A61B 17/0057 606/213 |
| 2007/0244517 | A1* | 10/2007 | Callaghan | A61B 17/0057 606/213 |
| 2007/0250081 | A1* | 10/2007 | Cahill | A61B 17/0057 606/151 |
| 2007/0250115 | A1* | 10/2007 | Opolski | A61B 17/0057 606/215 |
| 2008/0077180 | A1* | 3/2008 | Kladakis | A61B 17/0057 606/216 |
| 2008/0086168 | A1* | 4/2008 | Cahill | A61B 17/0057 606/213 |
| 2010/0185233 | A1* | 7/2010 | Thommen | A61B 17/0057 606/213 |
| 2012/0078295 | A1* | 3/2012 | Steiner | A61B 17/0057 606/213 |
| 2016/0074023 | A1* | 3/2016 | Sakamoto | A61B 17/0057 606/200 |
| 2016/0249898 | A1* | 9/2016 | Widmer | A61B 17/12122 606/213 |
| 2017/0156904 | A1* | 6/2017 | Liu | A61F 2/02 |
| 2018/0008248 | A1 | 1/2018 | Rafiee et al. | |
| 2018/0132856 | A1 | 5/2018 | Wierzbicki et al. | |
| 2018/0256139 | A1* | 9/2018 | Miller | A61F 6/22 |

FOREIGN PATENT DOCUMENTS

| | | |
|---|---|---|
| JP | 2019-17795 A | 2/2019 |
| JP | 2019-514647 A | 6/2019 |

* cited by examiner

412: Outer diameter D(3), Inner diameter d(3)
416

MEDICAL MATERIAL

TECHNICAL FIELD

The present invention relates to a medical material for treating a hole in biological tissue, and particularly relates to a medical material configured to be set in a catheter, sent to a treatment site through a blood vessel, and placed in a living body.

BACKGROUND ART

The heart of a human is divided into left and right chambers by tissue called the septum, and each of the left and right chambers has an atrium and a ventricle. That is, the heart is composed of two atria and two ventricles, i.e., right atrium, right ventricle, left atrium, and left ventricle. With regard to the heart having such a structure, atrial septal defect (ASD) is known, which is a defect wherein, due to a disorder of development in the fetal period, there is a congenital hole called a hole in the atrial septum separating the right atrium and the left atrium.

Treatment for atrial septal defect can be performed by the following two methods. One is a surgical operation performed by opening the chest, and the other is catheterization using an occluder without opening the chest.

A surgical operation (patching operation) involves using cardiopulmonary bypass, opening the chest, and closing the hole with a patch. Catheterization involves setting an occluder in a catheter, inserting the catheter into a blood vessel, sending the catheter to a target position (hole), and then releasing the occluder to place it in the body. The catheterization is to close a hole without opening the chest, by sending a small jig (device) called an occluder, folded in an elongated shape, from a vein (femoral vein) at the groin to the position of the hole in the atrial septum. The catheterization is advantageous in that the treatment can be performed merely by making a tiny skin incision (a few millimeters) in the groin (inguinal region), which is an inconspicuous area, without having to perform open chest surgery requiring general anesthesia.

Japanese Unexamined Patent Application Publication (Japanese translation of PCT International Application) No. 2008-512139 (Patent document 1) discloses an assembly (occluder) for use in catheterization for atrial septal defect. This assembly seals a passageway (hole) in the heart. The assembly includes: a closure device for sealing the passageway in the heart including a first anchor adapted to be placed proximate a first end of the passageway, a second anchor adapted to be placed proximate a second end of the passageway, and a flexible elongate member adapted to extend through the passageway and connect the first and second anchors, the second anchor capable of movement relative to the flexible elongate member to vary a length of the flexible elongate member between the first and second anchors; and a delivery system for delivering the closure device to the passageway in the heart, the delivery device being configured to move within a lumen of a guide catheter and including a wire configured to control movement of the second anchor along the flexible elongate material.

Patent document 1 also discloses that a patent foramen ovale (PFO) closure device (occluder) includes a left atrial anchor, a right atrial anchor, a tether, and a lock, and that the left atrial anchor, the right atrial anchor connected to the left atrial anchor via the tether, and the lock will remain in the heart to seal the PFO.

RELATED ART DOCUMENTS

Patent Documents

[Patent document 1] Japanese Unexamined Patent Application Publication (Japanese translation of PCT International Application) No. 2008-512139

DISCLOSURE OF THE INVENTION

Problems to be Solved by the Invention

A patching operation has an issue in that it involves usage of cardiopulmonary bypass, is highly invasive, and therefore requires long hospitalization. Catheterization is preferable because it does not involve usage of cardiopulmonary bypass, is less invasive, and therefore requires only short hospitalization.

As disclosed in Patent document 1, the left atrial anchor and the right atrial anchor remain in the heart. Each of the left and right atrial anchors includes one or more arms, which extend radially outward from a hub. The arms are preferably formed from a rolled sheet of binary nickel titanium alloy. A hole is to be closed by extending the left atrial anchor and the right atrial anchor in a living body; however, once the extension of the anchors has been started, it is difficult to bring the anchors into their original state. The anchors are to be folded by means of a dedicated takeout device which has a complicated structure and which is difficult to operate from outside the living body, as disclosed in Patent document 1.

However, for example, in the event that an anchor has accidentally been caught in biological tissue within an atrium and damaged the biological tissue, there may be cases where there is not enough time to fold the anchor using such a dedicated takeout device. In such a case, there is no other choice but to perform open chest surgery immediately. Under such circumstances, the patient will end up with highly invasive open chest surgery, which is an issue.

There is another issue in that a hole occluder made of metal will remain in the body for the whole life and that some problem may occur in the late post-treatment period.

The present invention was made in view of the above-mentioned issues of the conventional techniques, and its object is to provide a medical material which makes it possible to perform less invasive catheterization capable of releasing and placing the medical material at a treatment site inside a living body with easy and reliable operation without a complicated structure and which is unlikely to cause problems in the late post-treatment period even when remaining in the body.

Means of Solving the Problems

In order to attain the above object, a medical material according to an aspect of the present invention employs the following technical means.

Specifically, a medical material according to the present invention is a medical material comprised of a tubular body that has a mesh structure formed of a bioabsorbable linear material, wherein: the medical material has a shape in which a substantially middle portion of the tubular body is smaller in tube diameter than other portions of the tubular body; the medical material has a first tubular portion with a first end and a second tubular portion with a second end which are arranged with the substantially middle portion therebetween, the first end and the second end being opposite ends in a longitudinal direction of the tubular body; when the medical material is contained in a catheter such that the first end and the second end are away from each other with the substantially middle portion therebetween and that the other portions have a reduced tube diameter, the second end is located on the same side of the catheter as a distal end of the catheter; the medical material includes, at the second end, a connecting part configured to have connected thereto a delivery cable that passes through the medical material from the first end via the substantially middle portion toward the second end; and the medical material is configured to allow the delivery cable to pass out of the medical material through the first end.

It is preferable that the medical material can be configured such that the connecting part is a hollow cylindrical object which has an internal thread and to which the delivery cable is connected by screwing an external thread at a distal end of the delivery cable into the internal thread.

It is more preferable that the medical material can be configured such that the hollow cylindrical object has: an open end which is on the same side of the hollow cylindrical object as the first tubular portion, which has the internal thread, and which is capable of being screwed onto the external thread; and a closed end which is on the opposite side of the hollow cylindrical object from the first tubular portion.

It is more preferable that the medical material can be configured such that, while the medical material connected by the connecting part to the delivery cable is entirely contained in the catheter, the delivery cable is manipulated such that the medical material advances in a direction toward an opening of the catheter, and the second tubular portion is allowed to move out of the catheter through the distal end of the catheter and then the first tubular portion is allowed to move out of the catheter through the distal end of the catheter, so that the first end and the second end come close to each other with the substantially middle portion therebetween and the other portions increase in tube diameter to a size corresponding to a hole to be closed with the medical material.

It is more preferable that the medical material can be configured such that the medical material further includes a loop which has one end connected to the first end and which has the opposite end connected to an anti-falling member having a size larger than an inner diameter of the catheter, wherein an overall length of the loop is greater than an overall length of the catheter.

In order to attain the above object, a medical material according to another aspect of the present invention employs the following technical means.

Specifically, a medical material according to the present invention is a medical material comprised of a tubular body that has a mesh structure formed of a bioabsorbable linear material, wherein: the medical material has a shape in which a substantially middle portion of the tubular body is smaller in tube diameter than other portions of the tubular body; the medical material has a first tubular portion with a first end and a second tubular portion with a second end which are arranged with the substantially middle portion therebetween, the first end and the second end being opposite ends in a longitudinal direction of the tubular body; when the medical material is contained in a catheter such that the first end and the second end are away from each other with the substantially middle portion therebetween and that the other portions have a reduced tube diameter, the second end is located on the same side of the catheter as a distal end of the catheter; the medical material includes: a proximal connecting part connected to the mesh structure at the first end; and a distal connecting part connected to the mesh structure at the second end; the proximal connecting part and the distal connecting part each have a hollow tubular shape, and are capable of selectively achieving: "locked" in which the proximal connecting part and the distal connecting part remain united; and "unlocked" in which the proximal connecting part and the distal connecting part do not remain united; an inner diameter of the proximal connecting part is larger than an outer diameter of a delivery cable inserted in the catheter; the distal connecting part is capable of selectively achieving a connected state in which the distal connecting part is connected to a distal end of the delivery cable and a disconnected state in which the distal connecting part is not connected to the distal end of the delivery cable; and the medical material is configured to allow the delivery cable, which has the distal end thereof connected to the distal connecting part, to pass through the substantially middle portion, be inserted into a hollow tube of the proximal connecting part, and pass out of the medical material in a direction from the second end to the first end.

It is preferable that the medical material can be configured such that: the distal connecting part is a hollow tubular object having an internal thread; the delivery cable has, at the distal end thereof, an external thread configured to be screwed into the internal thread; the connected state is achieved by screwing the external thread into the internal thread, and the disconnected state is achieved by unscrewing the external thread from the internal thread; and the medical material is configured such that the external thread and the internal thread are capable of being unscrewed from each other while the proximal connecting part and the distal connecting part remain united and locked.

It is more preferable that the medical material can be configured such that: the proximal connecting part and the distal connecting part each have a hollow cylindrical shape; an outer diameter of the distal connecting part is smaller than the inner diameter of the proximal connecting part; the distal connecting part has a recess in an outer peripheral surface thereof; the proximal connecting part has, on an inner peripheral surface thereof, a protrusion configured to engage with the recess; and engagement between the recess and the protrusion causes the proximal connecting part and the distal connecting part to be united and locked.

It is more preferable that the medical material can be configured such that: a shape of the recess in the outer peripheral surface of the distal connecting part has a groove shape provided along a circumferential direction, and a length of the groove shape along the circumferential direction is less than an outer circumference of the distal connecting part; a shape of the protrusion on the inner peripheral surface of the proximal connecting part is a short shaft shape that extends from the inner peripheral surface toward a cylinder central axis; a groove width of the groove shape and a shaft diameter of the short shaft shape are substantially equal to each other; and engagement of a shaft portion of the short shaft shape with a groove portion of the groove shape causes the proximal connecting part and the distal connecting part to be united and locked.

It is more preferable that the medical material can be configured such that the medical material is configured such that the external thread and the internal thread are capable of being unscrewed from each other while the proximal connecting part and the distal connecting part remain united and locked because: the groove shape along the circumferential direction has an area which allows the shaft to be more tightly engaged with decreasing distance to an innermost end of the groove along the circumferential direction; the groove shape along the circumferential direction has an area which has a narrow groove width to allow the shaft to be tightly engaged and which is provided near the innermost end of the groove along the circumferential direction; or the groove shape along the circumferential direction has, near the innermost end of the groove along the circumferential direction, at least one bend at which the groove shape bends from the circumferential direction to another direction other than the circumferential direction.

It is more preferable that the medical material can be configured to achieve the following: while the medical material in which the distal end of the delivery cable is connected to the second end by the distal connecting part is entirely contained in the catheter, the delivery cable is manipulated, and the second tubular portion is allowed to move out of the catheter through the distal end of the catheter and then the first tubular portion is allowed to move out of the catheter through the distal end of the catheter such that the medical material advances in a direction toward an opening of the catheter, so that the first end and the second end come close to each other with the substantially middle portion therebetween; the delivery cable is manipulated and the proximal connecting part and the distal connecting part are united and locked so that the proximal connecting part and the distal connecting part remain united, thereby maintaining a state in which the other portions have a tube diameter increased to a size corresponding to a hole to be closed with the medical material; and the delivery cable is manipulated, the distal connecting part and the distal end of the delivery cable are disconnected, and the catheter, together with the delivery cable inserted in the catheter, is separated from a site where there is the hole.

Effects of the Invention

A medical material according to the present invention makes it possible to perform less invasive catheterization capable of releasing and placing the medical material at a treatment site in a living body with easy and reliable operation without a complicated structure. Furthermore, the medical material according to the present invention is unlikely to cause problems in the late post-treatment period even when remaining in the body.

BEST MODE FOR CARRYING OUT THE INVENTION

Figure 1A:
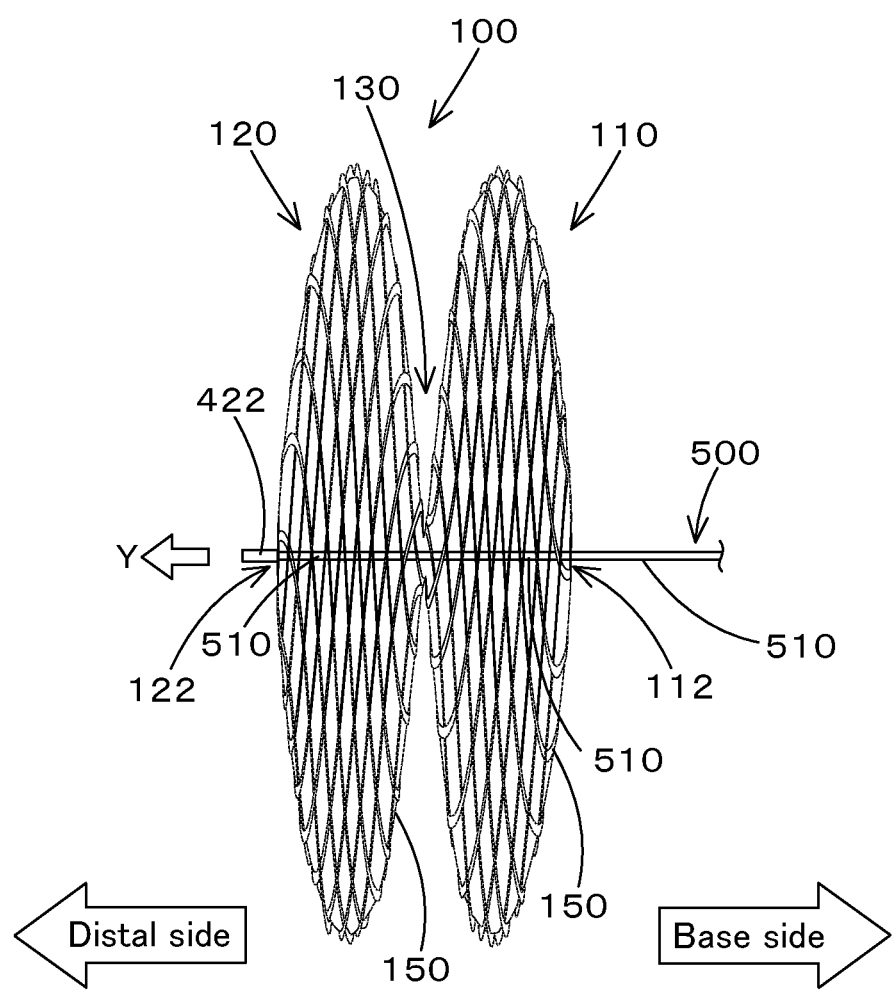
FIG. 1A is an overall view of a hole closing material 100 which is an example of a medical material according to the present invention (state in which a first end and a second end are close to each other).
Figure 1B:
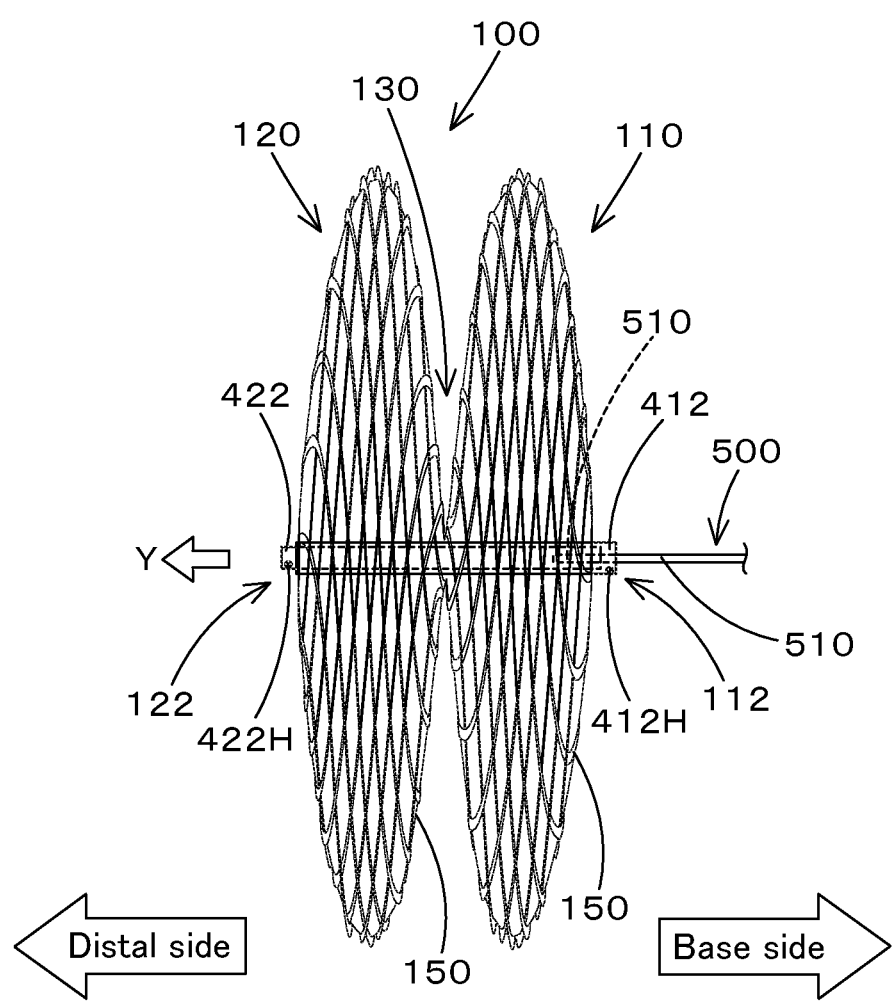
FIG. 1B is an overall view of a hole closing material 100 which is another example of a medical material according to the present invention (state in which the first end and the second end are close to each other).

The following description discusses a medical material according to the present invention in detail with reference to the drawings. Although the following description discusses a hole closing material for use in catheterization as an example of the medical material according to the present invention, the medical material is suitably applicable also to closure of other openings or passageways including, for example, other openings in the heart such as ventricular septal defect and patent ductus arteriosus and openings or passageways in other parts of a living body (for example, stomach) such as arteriovenous fistula. As such, the hole closing material according to an embodiment of the present invention is not limited to be used for the closure of a hole of atrial septal defect.

Moreover, although the description in the following embodiment is based on the assumption that a mesh structure of a hole closing material (occluder) 100 which is an example of a medical material according to the present invention is knitted or woven from bioabsorbable fiber (an example of a linear material), the present invention is not limited thereto. It is only necessary that the hole closing material enable catheterization to close a hole in a living body, and its mesh structure and material are not limited, provided that the mesh structure and material have first to third features described later and achieve first to fourth effects described later. With regard to the material, for example, the hole closing material may be knitted or woven from a linear material other than the bioabsorbable fiber. Such a linear material is preferably a linear material having a certain degree of hardness to achieve form retaining property (shape retaining property) of the hole closing material. Note that "FIG. N (N is an integer of 1 to 14 excluding 6 and 10)" (i.e., FIGS. 1 to 14 referenced in the following description, except for FIGS. 6 and 10) have a suffix A, B, or the like indicating a corresponding drawing, which is in the form of FIG. NA, FIG. NB, or the like; however, in the following description, if a passage includes "FIG. N" alone, that passage is commonly applicable to FIGS. NA, NB, and the like.

Basic Configuration

FIG. 1 shows an overall view of the hole closing material 100 according to the present embodiment (state in which a first end 112 and a second end 122 are close to each other), FIG. 2 shows another overall view of the hole closing material 100 (the distance between the first end 112 and the second end 122 is in an intermediate state), FIG. 3 shows a further overall view of the hole closing material 100 (the hole closing material 100 is entirely contained in a catheter 300, and the first end 112 and the second end 122 are away from each other), and FIG. 4 shows still a further overall view of the hole closing material 100 (state in which a second tubular portion 120 has been moved out of the catheter 300 and the first tubular portion 110 is contained in the catheter 300). Note that, with regard to the relationship between the hole closing material 100 and the catheter 300 in which the hole closing material 100 is contained, FIG. 3 illustrates the hole closing material 100 which is entirely contained in the catheter 300, and FIG. 4 illustrates the hole closing material 100 which is half (first tubular portion 110) contained in the catheter 300.

In terms of temporal transition, when the second tubular portion 120 of the hole closing material 100 which is entirely contained in the catheter 300 (in the space defined by an inner wall 310) illustrated in FIG. 3 is allowed to move out through an opening 320 of the catheter 300 in the direction indicated by an arrow Y, the state of FIG. 4 results, and, when the first tubular portion 110 is also allowed to move out in the direction indicated by the arrow Y, the state of FIG. 1 results. It is noted here that the state of the hole closing material 100 illustrated in FIG. 2 is an imaginary state where the distance between the first end 112 and the second end 122 is in an intermediate state. FIG. 13 is an enlarged view including a distal connecting part 422 provided at the distal end (second end 122) and a proximal connecting part 412 provided at the proximal end (first end 112) of the hole closing material 100 and a delivery cable 500 which is screwed to the distal connecting part 422. FIG. 14 is a perspective view of them. Note that the terms "proximal" and "base" are synonymous.

As illustrated in these drawings, an overview of the hole closing material 100 is as follows: the hole closing material 100 is comprised of a tubular body that has a mesh structure formed of a linear material, the hole closing material 100 has a shape in which a substantially middle portion 130 of the tubular body is smaller in tube diameter than other portions of the tubular body, the hole closing material 100 has a first tubular portion 110 with a first end 112 and a second tubular portion 120 with an opposite end (second end 122) which are arranged with the substantially middle portion 130 therebetween, the first end 112 and the opposite end being opposite ends of the hole closing material 100 in a longitudinal direction of the tubular body.

Figure 2A:
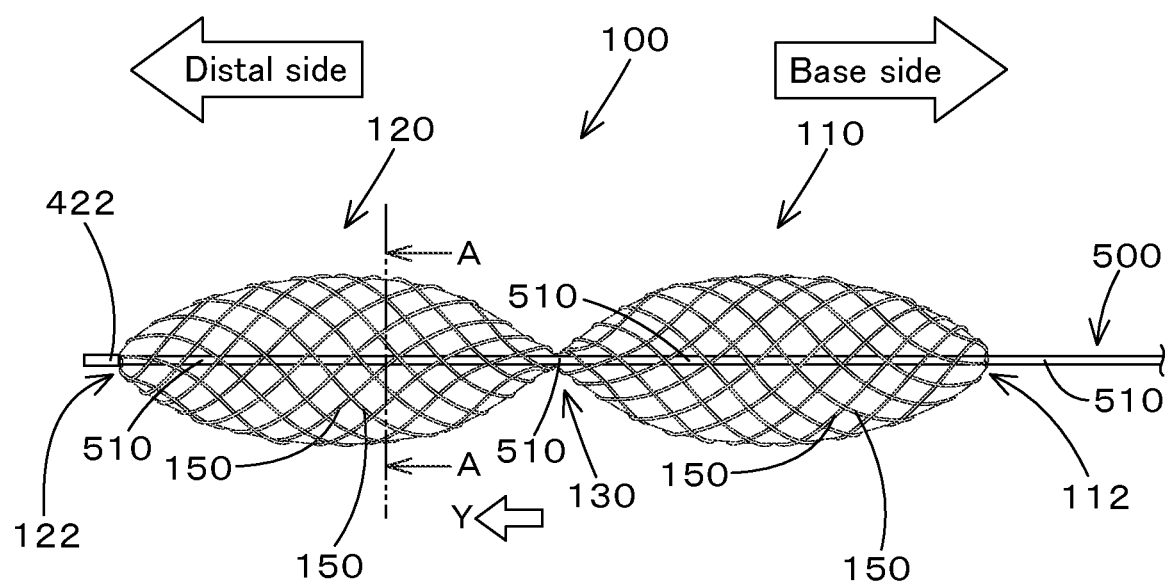
FIG. 2A is an overall view of the hole closing material 100 illustrated in FIG. 1A (the distance between the first end and the second end is in an intermediate state).
Figure 3A:
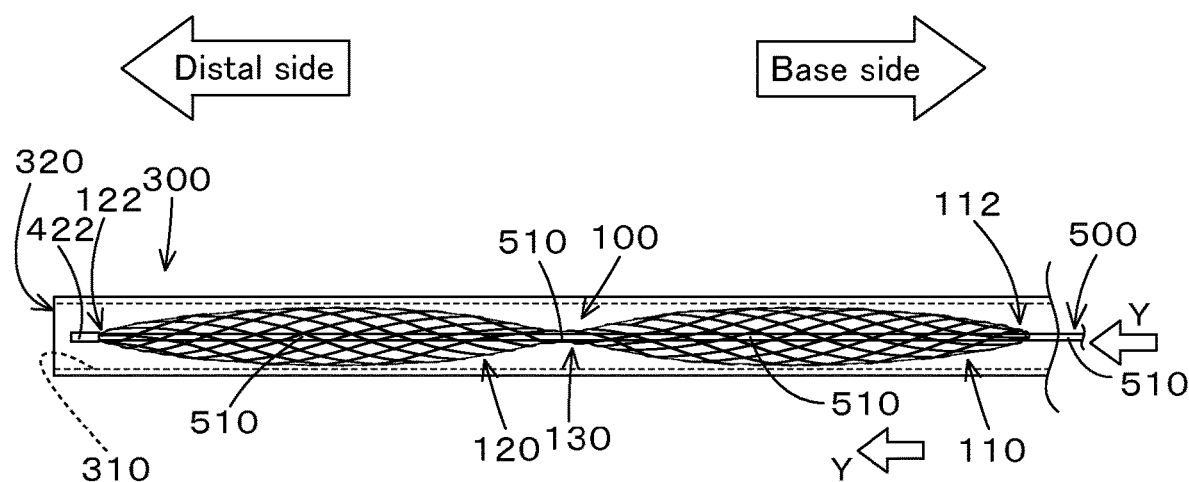
FIG. 3A is an overall view of the hole closing material 100 illustrated in FIG. 1A (the hole closing material is entirely contained in a catheter 300 and the first end and the second end are away from each other).
Figure 3B:
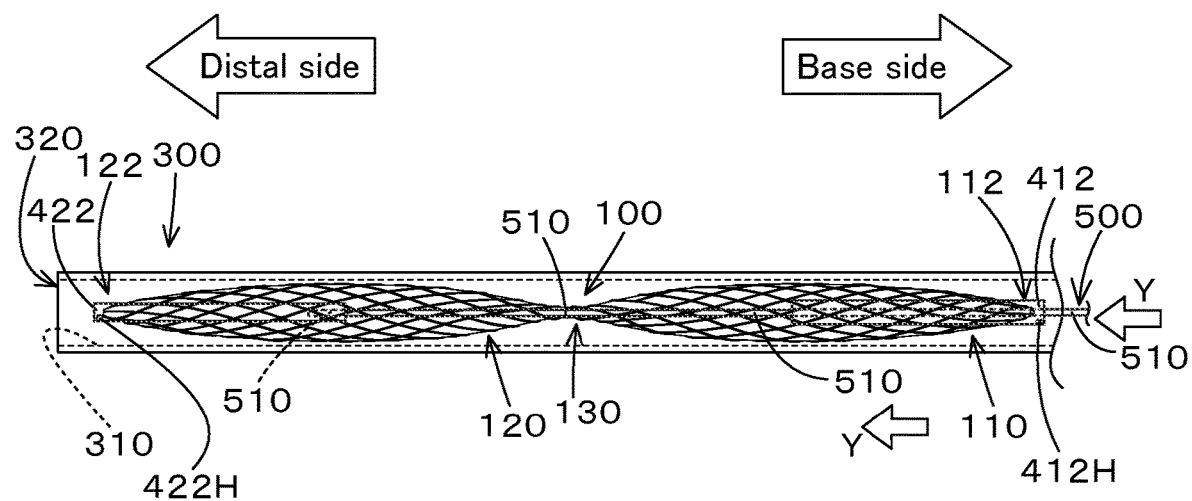
FIG. 3B is an overall view of the hole closing material 100 illustrated in FIG. 1B (the hole closing material is entirely contained in the catheter 300 and the first end and the second end are away from each other).
Figure 4A:
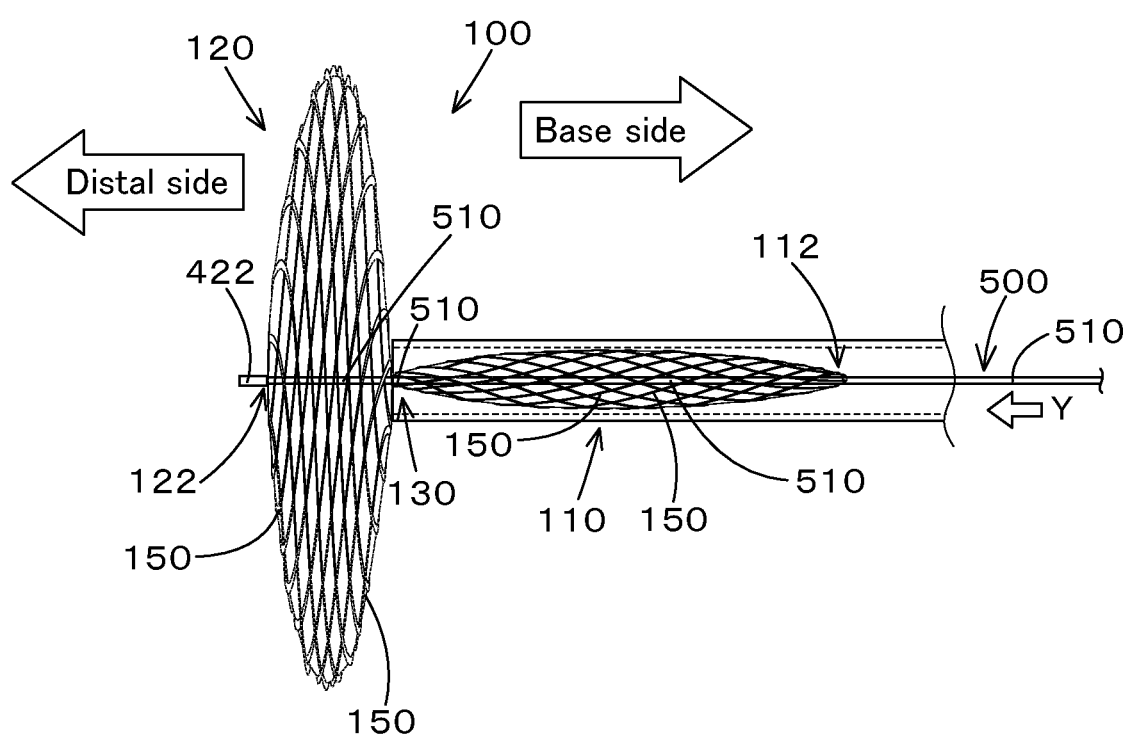
FIG. 4A is an overall view of the hole closing material 100 illustrated in FIG. 1A (state in which a second tubular portion has been moved out of the catheter 300 and a first tubular portion is contained in the catheter 300).
Figure 4B:
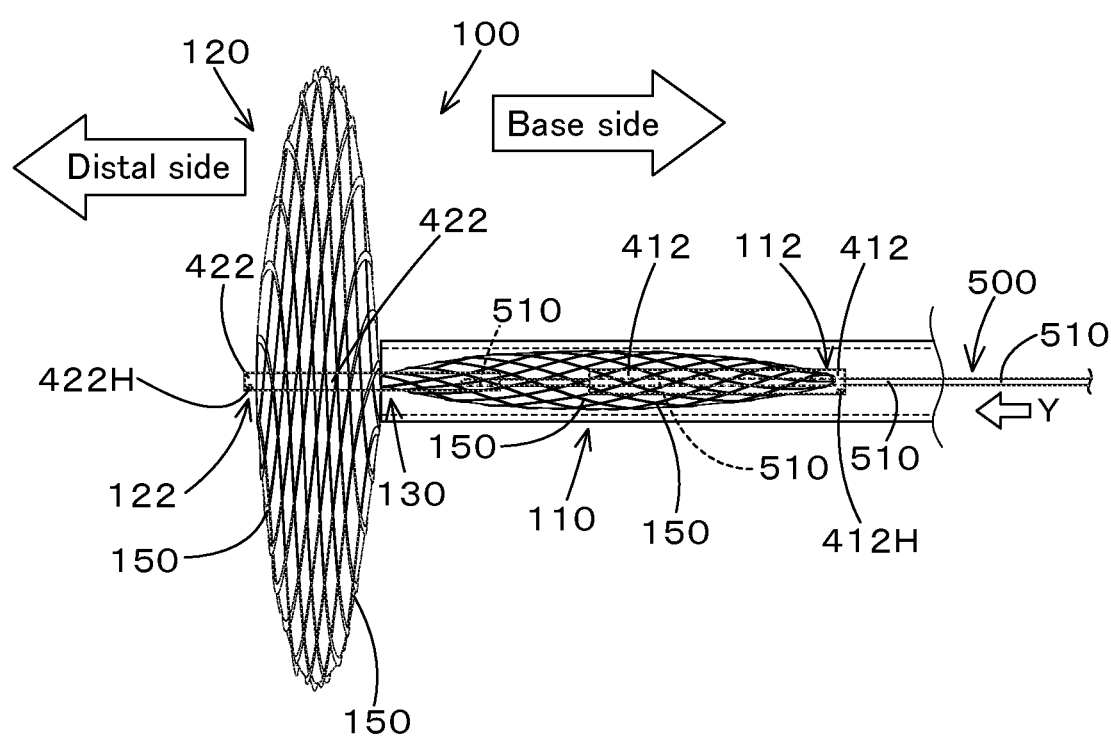
FIG. 4B is an overall view of the hole closing material 100 illustrated in FIG. 1B (state in which the second tubular portion has been moved out of the catheter 300 and the first tubular portion is contained in the catheter 300).

The hole closing material 100 is characterized in that, as illustrated in FIGS. 1A, 2A, 3A, 4A, 5A, and 5B, when the hole closing material 100 is contained in the catheter 300 such that the first end 112 and the second end 122 are away from each other with the substantially middle portion 130 therebetween and that the other portions have a reduced tube diameter (the state as illustrated in FIG. 3), the second end 122 is located on the same side of the catheter 300 as the distal end of the catheter 300. In such a case, the hole closing material 100 includes, at the second end 122, the distal connecting part 422 configured to have connected thereto a manipulation wire 500 (which may be hereinafter referred to as "delivery cable 500") that passes through the hole closing material 100 from the first end 112 via the substantially middle portion 130 toward the second end 122. Furthermore, the hole closing material 100 is configured to allow the delivery cable 500 to pass out of the hole closing material 100 through the first end 112 (for example, the first end 112 has a hole that allows passage of a cable body 510 of the delivery cable 500).

Figure 10:
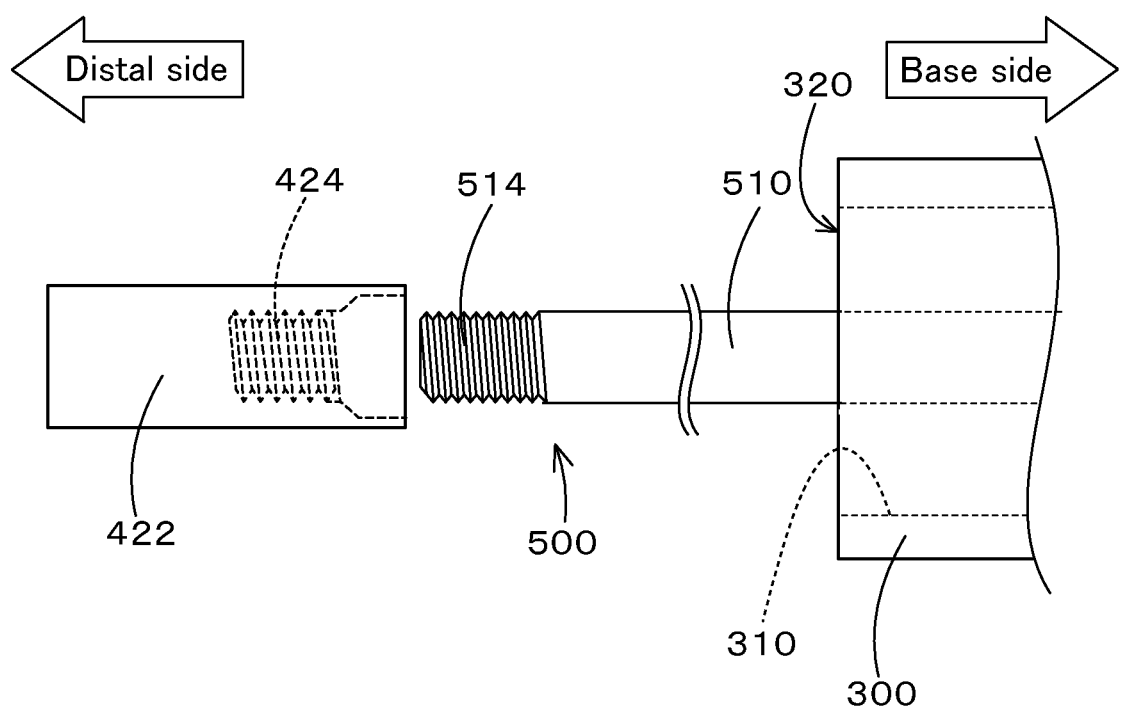
FIG. 10 is an enlarged view of a distal connecting part 422 provided at the distal end of the hole closing material 100 and a delivery cable 500 screwed to the distal connecting part 422.
Figure 11A:
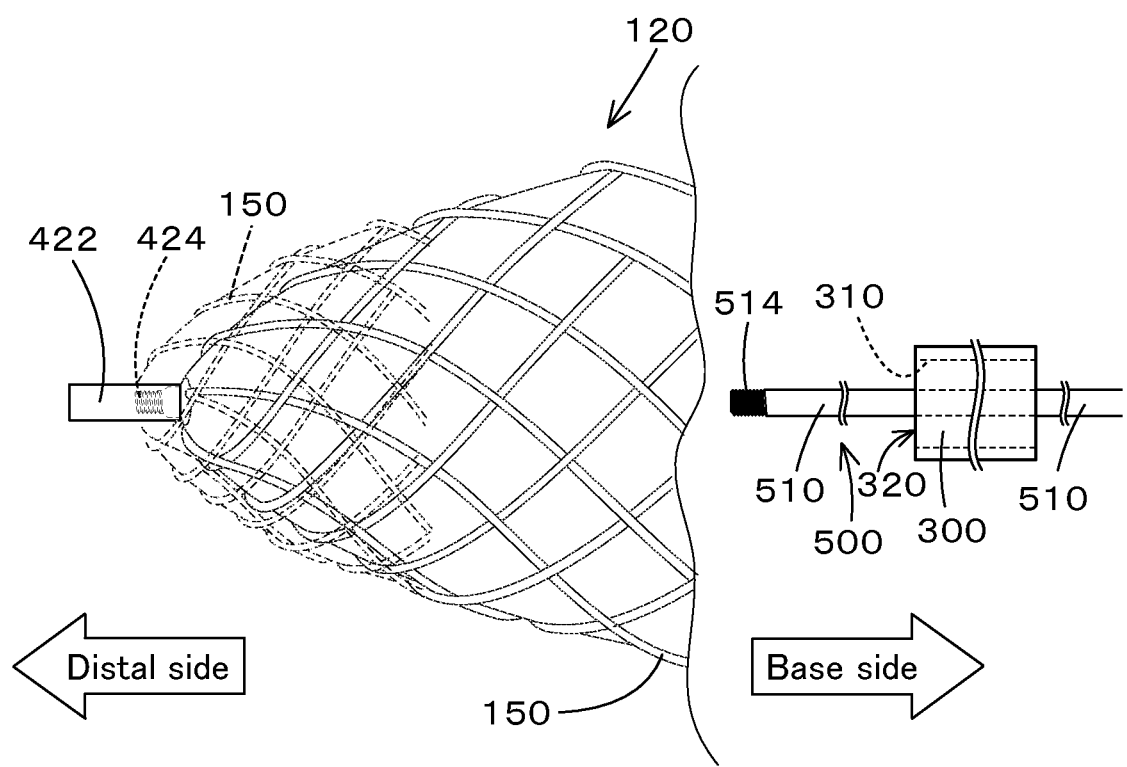
FIG. 11A is an enlarged view of the catheter 300 which includes the distal end (second end 122) of the hole closing material 100 and the delivery cable 500 illustrated in FIG. 1A.
Figure 11B:
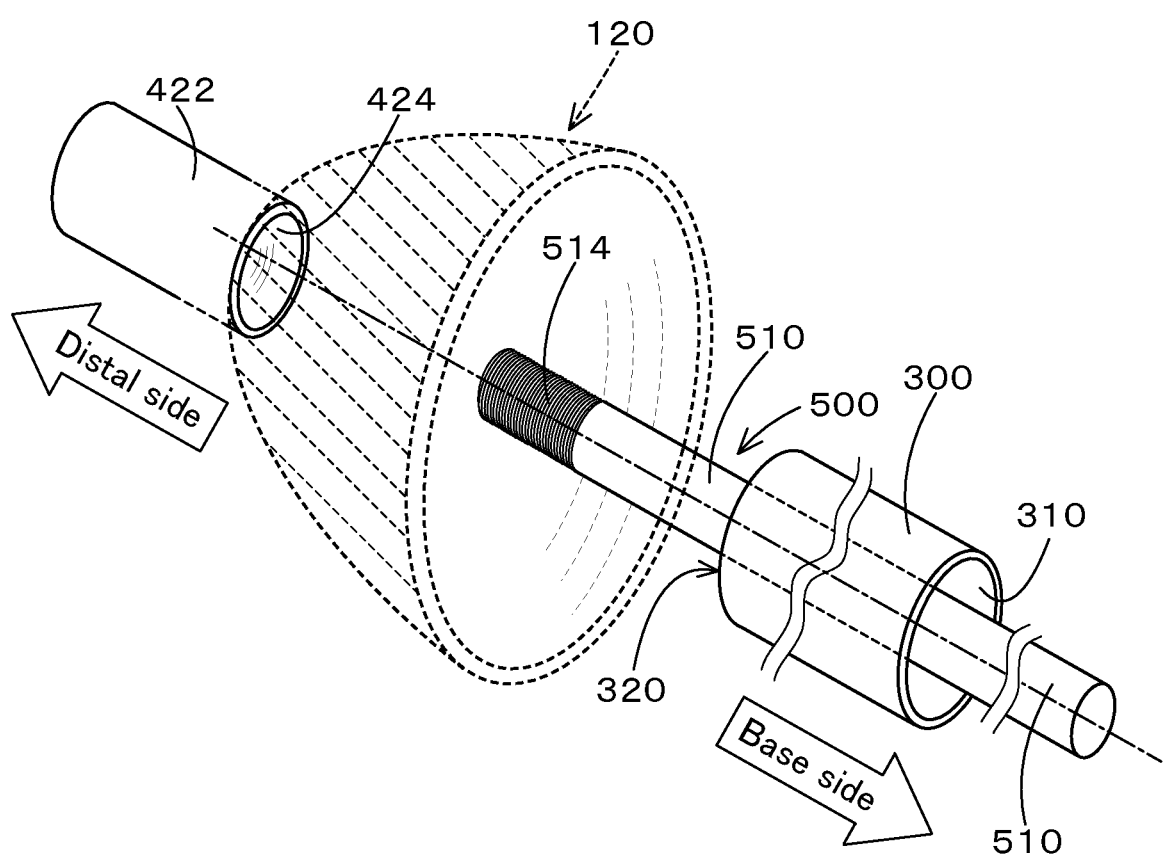
FIG. 11B is a perspective view of FIG. 11A.

It is noted here that, as illustrated in FIGS. 10 and 11, the distal connecting part 422 is a hollow cylindrical object (made of, for example, metal) having an internal thread 424, to which the cable body 510 of the delivery cable 500 is connected by screwing an external thread 514 at the distal end of the cable body 510 into the internal thread 424. Note that, in the living body, by turning the cable body 510 (rotating the cable body 510 on its axis) in the direction opposite to the direction in which the external thread 514 is screwed into the internal thread 424, it is possible to undo the screwed connection and separate the hole closing material 100 and the delivery cable 500.

It is noted here that, as illustrated in FIGS. 10 and 11, the hollow cylindrical object forming the distal connecting part 422 has: an open end which is on the same side of the hollow cylindrical object as the first tubular portion 110, which has the internal thread 424, and which is capable of being screwed onto the external thread 514 provided at the distal end of the cable body 510 of the delivery cable 500; and a closed end which is on the opposite side of the hollow cylindrical object from the first tubular portion 110.

The end which is on the opposite side of the hollow cylindrical object from the first tubular portion 100 is preferably closed as such, because the delivery cable can be easily manipulated and the hole closing material can be prevented from twisting when the hole closing material is forced to advance within a sheath.

Note that the hole closing material 100 is configured as follows, details of which will be described later in [Usage Embodiments]: while the hole closing material 100 connected by the distal connecting part 422 to the delivery cable 500 is entirely contained in the catheter 300, the delivery cable 500 is manipulated (such that the hole closing material 100 advances in the direction toward the opening 320 of the catheter 300) and the second tubular portion 120 is allowed to move out of the catheter 300 through the distal end of the catheter and then the first tubular portion 110 is allowed to move out of the catheter 300 through the distal end of the catheter, so that the first end 112 and the second end 122 come close to each other with the substantially middle portion 130 therebetween and the other portions increase in tube diameter to a size corresponding to the hole to be closed with the hole closing material 100.

In so doing, since the distal connecting part 422 is located at the second end 122 and the distal end of the delivery cable 500 is connected to the distal connecting part 422, the second tubular portion 120 and the first tubular portion 110 are not pushed out of the catheter 300 (such as cases where the distal connecting part 422 connected to the distal end of the delivery cable 500 is located at the first end 122) but moved out of the catheter 300 in a manner such that the second tubular portion 120 and the first tubular portion 110 are pulled. If the second tubular portion 120 and the first tubular portion 110 are pushed out of the catheter 300, there may be cases where the hole closing material 100 is twisted, the first end 112 and the second end 122 cannot appropriately come close to each other with the substantially middle portion 130 therebetween, and the other portions do not appropriately increase in tube diameter to a size corresponding to the hole to be closed with the hole closing material 100. However, when the second tubular portion 120 and the first tubular portion 110 are pulled, the twisting of the hole closing material 100 is prevented or reduced, the first end 112 and the second end 122 appropriately come close to each other with the substantially middle portion 130 therebetween, and the other portions can appropriately increase in tube diameter to a size corresponding to the hole to be closed with the hole closing material 100.

Figure 5A:
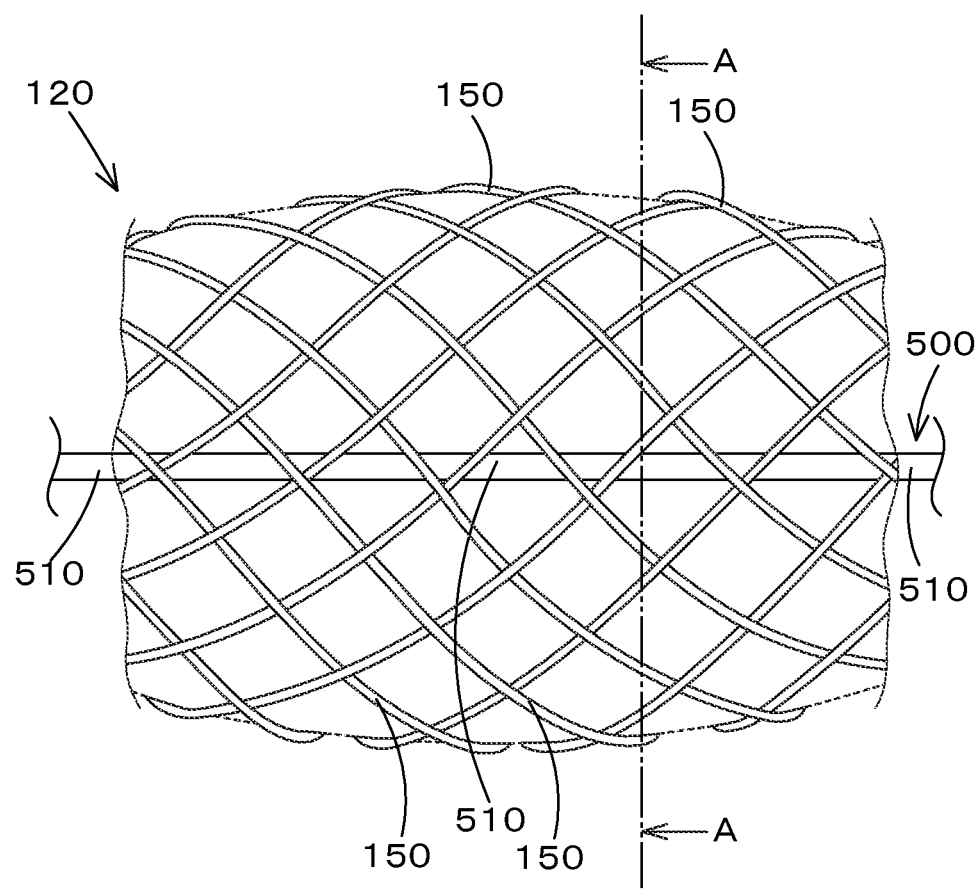
FIG. 5A is a partial side view of the hole closing material 100 in the state shown in FIG. 2A.
Figure 5B:
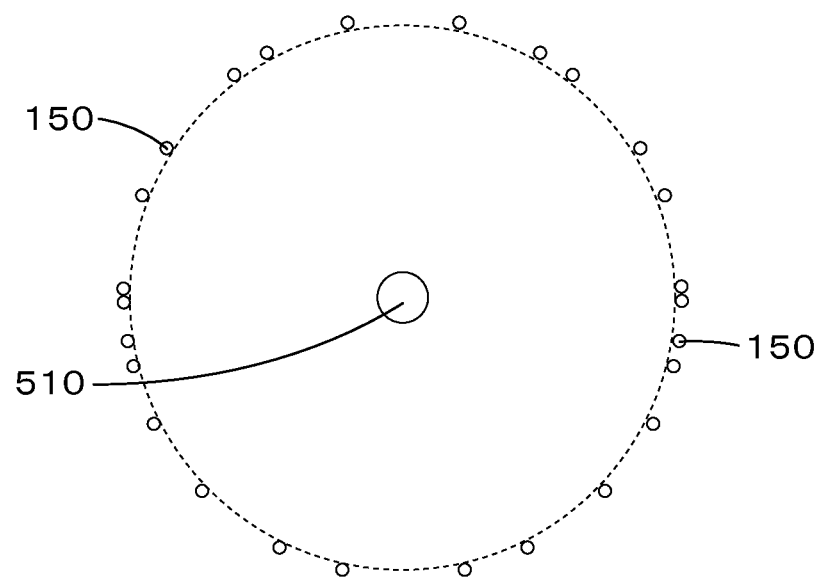
FIG. 5B is a cross-sectional view taken along A-A in FIG. 5A.

Furthermore, FIG. 5A is a partial side view of the hole closing material 100 illustrated in FIGS. 1A, 2A, 3A, and 4A, and FIG. 5B is a cross-sectional view taken along A-A in FIGS. 2A and 5A. Note that although FIG. 5B is a cross-sectional view of the hole closing material 100 (more specifically, the second tubular portion 120), FIG. 5B illustrates a cross-section of the cable body 510 of the delivery cable 500 and does not illustrate the mesh of a bioabsorbable fiber 150 that is visible from a direction indicated by an arrow A. Furthermore, in FIGS. 1A, 2A, 3A, 4A, 5A, and 5B, the bioabsorbable fiber 150 disposed on the far side of each drawing is not illustrated in order to facilitate the understanding of the presence of the cable body 510 of the delivery cable 500 located inside the hole closing material 100 and the mesh of the bioabsorbable fiber 150, and there are some areas in which the external shape of the hole closing material 100 is represented by a dashed line in order to facilitate the understanding of the external shape of the hole closing material 100.

Furthermore, the hole closing material 100 is characterized in that, as illustrated in FIGS. 1B, 2B, 3B, 4B, 5C, and 5D, when the hole closing material 100 is contained in the catheter 300 such that the first end 112 and the second end 122 are away from each other with the substantially middle portion 130 therebetween and the other portions have a reduced tube diameter (the state illustrated in FIG. 3), the second end 122 is located on the same side of the catheter 300 as the distal end of the catheter 300. In such a case, the hole closing material 100 includes: the proximal connecting part 412 connected to the mesh structure at the first end 112; and the distal connecting part 422 connected to the mesh structure at the second end 122. Note that a non-limiting configuration is as follows: for example, a part of the bioabsorbable fiber 150 forming the first tubular portion 110 is passed through a hole 412H in the proximal connecting part 412 and the part of the bioabsorbable fiber 150 thus passed through the hole 412H is tied together with another part of the bioabsorbable fiber 150 that is not passed through the hole 412H, thereby connecting the proximal connecting part 412 to the mesh structure at the first end 112; and, for example, a part of the bioabsorbable fiber 150 forming the second tubular portion 120 is passed through a hole 422H in the distal connecting part 422 and the part of the bioabsorbable fiber 150 thus passed through the hole 422H is tied together with another part of the bioabsorbable fiber 150 that is not passed through the hole 422H1, thereby connecting the distal connecting part 422 to the mesh structure at the second end 122.

The proximal connecting part 412 and the distal connecting part 422 each have a hollow tubular shape, and are configured to be capable of selectively achieving: "locked" in which the proximal connecting part 412 and the distal connecting part 422 remain united; and "unlocked" in which the proximal connecting part 412 and the distal connecting part 422 do not remain united. An inner diameter d(3) of the proximal connecting part 412 is larger than an outer diameter D(2) of the manipulation wire 500 (hereinafter may be referred to as "delivery cable 500") inserted in the catheter 300, and the distal connecting part 422 is configured to be capable of selectively achieving a connected state in which the distal connecting part 422 is connected to the distal end of the delivery cable 500 and a disconnected state in which the distal connecting part 422 is not connected to the delivery cable 500. The hole closing material 100 is configured to allow the delivery cable 500, which has the distal end thereof connected to the distal connecting part 422, to pass through the substantially middle portion 130, be inserted into a hollow tube of the proximal connecting part 412, and pass out of the hole closing material 100 in a direction from the second end 122 to the first end 112 (for example, the first end 112 has a hole that allows passage of the cable body 510 of the delivery cable 500).

More specifically, the distal connecting part 422 may be a hollow tubular object (made of, for example, metal) having the internal thread 424. The hollow tubular shape of the distal connecting part 422 means that the internal thread 424 is provided to form a hollow space. In such a case, the delivery cable 500 has, at the distal end thereof, the external thread 514 configured to be screwed into the internal thread 424. Note that the distal end of the delivery cable 500 is synonymous with the distal end of the cable body 510. The foregoing connected state is achieved by screwing the external thread 514 into the internal thread 424, and the foregoing disconnected state is achieved by unscrewing the external thread 514 from the internal thread 424. Thus, the hole closing material 100 is configured such that the external thread 514 and the internal thread 424 can be unscrewed from each other while the proximal connecting part 412 and the distal connecting part 422 are united and locked as described earlier.

More specifically, the proximal connecting part 412 and the distal connecting part 422 may each have a hollow cylindrical shape. The hollow cylindrical shape of the distal connecting part 422 means that the internal thread 424 is provided in a distal connecting part's main body 422B having a cylindrical shape to form a hollow space. In such a case, the outer diameter of the distal connecting part 422 (more specifically, outer diameter D(5) of a lock groove cover 422C of the distal connecting part 422) is (slightly) smaller than the inner diameter d(3) of the proximal connecting part 412. The distal connecting part 422 has a recess (more specifically, lock groove 426) in the outer peripheral surface thereof (more specifically, the peripheral surface of the lock groove cover 422C of the distal connecting part 422), and the proximal connecting part 412 has, on the inner peripheral surface thereof, a protrusion (more specifically, a lock pin 416 in the form of a short shaft) configured to engage with the recess (lock groove 426). The hole closing material 100 is configured such that the engagement between the recess (lock groove 426) and the protrusion (lock pin 416) causes the proximal connecting part 412 and the distal connecting part 422 to be united and locked.

More specifically, the shape of the recess (lock groove 426) in the outer peripheral surface of the distal connecting part 422 has a groove shape provided along the circumferential direction, and the length of the groove shape along the circumferential direction is less than the outer circumference of the distal connecting part. The shape of the protrusion (lock pin 416) on the inner peripheral surface of the proximal connecting part 412 may be a short shaft shape that extends from the inner peripheral surface toward the cylinder central axis. In such a case, the hole closing material 100 is configured such that: a groove width M of the groove shape and a shaft diameter N of the short shaft shape are substantially equal to each other; and engagement of a shaft portion (lock pin 416) of the short shaft shape with a groove portion (lock groove 426) of the groove shape causes the proximal connecting part 412 and the distal connecting part 422 to be united and locked.

Figure 13A:
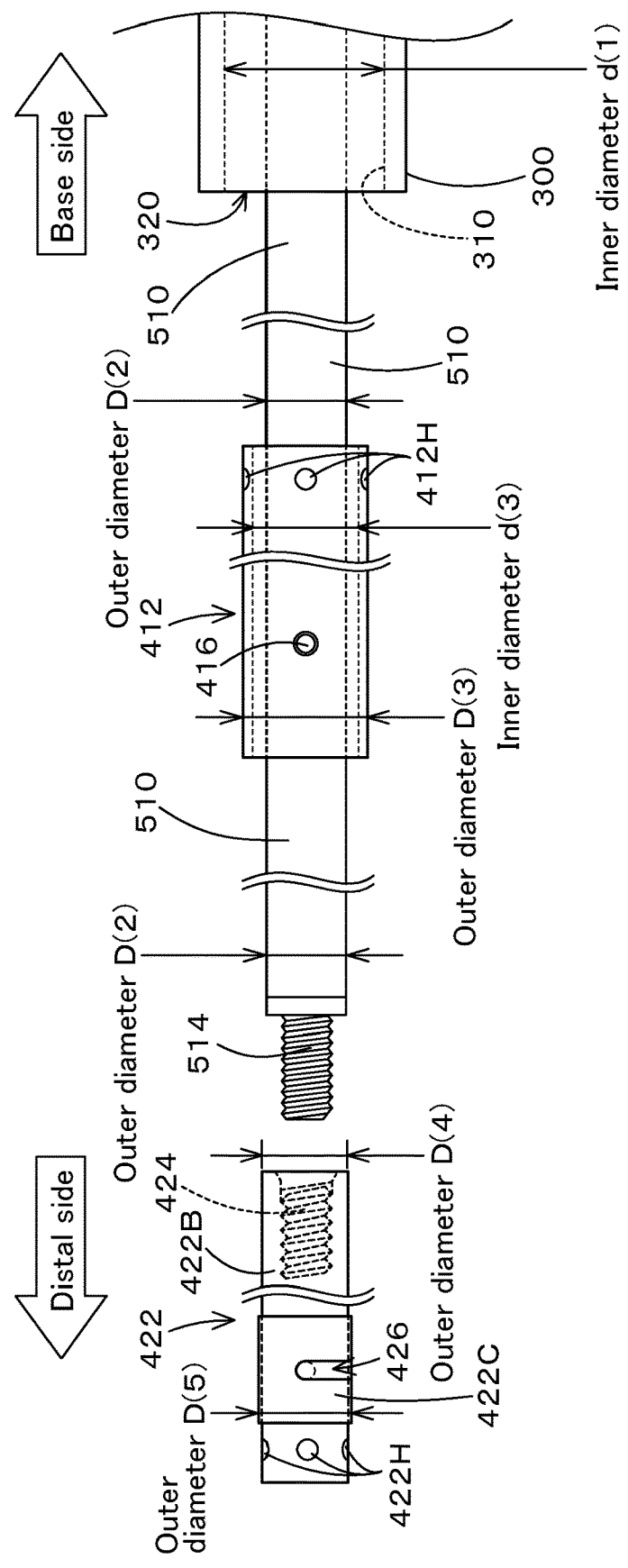
FIG. 13A is an enlarged view including a distal connecting part 422 provided at the distal end (second end 122) and a proximal connecting part 412 provided at the proximal end (first end 112) of the hole closing material 100 illustrated in FIG. 1B, and a delivery cable 500 which is screwed to the distal connecting part 422.
Figure 13B:
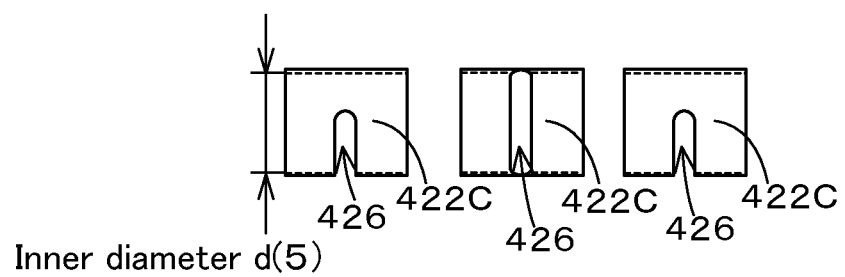
FIG. 13B shows partial views (1) of FIG. 13A.
Figure 13C:
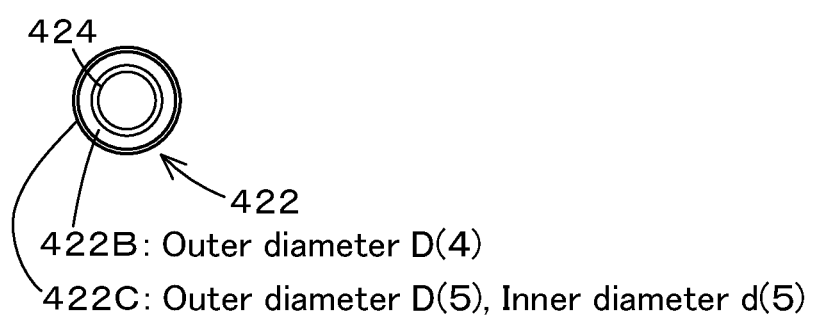
FIG. 13C is a partial view (2) of FIG. 13A.
Figure 13D:
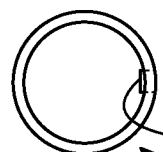
FIG. 13D is a partial view (3) of FIG. 13A.
Figure 13E:
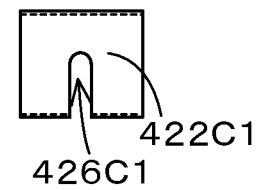
FIG. 13E is a partial view (4) of FIG. 13A.
Figure 13F:
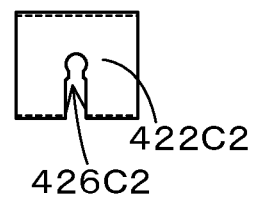
FIG. 13F is a partial view (5) of FIG. 13A.
Figure 13G:
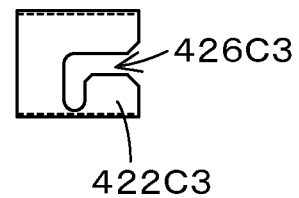
FIG. 13G is a partial view (6) of FIG. 13A.
Figure 13H:
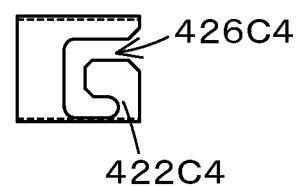
FIG. 13H is a partial view (7) of FIG. 13A.
Figure 13I:
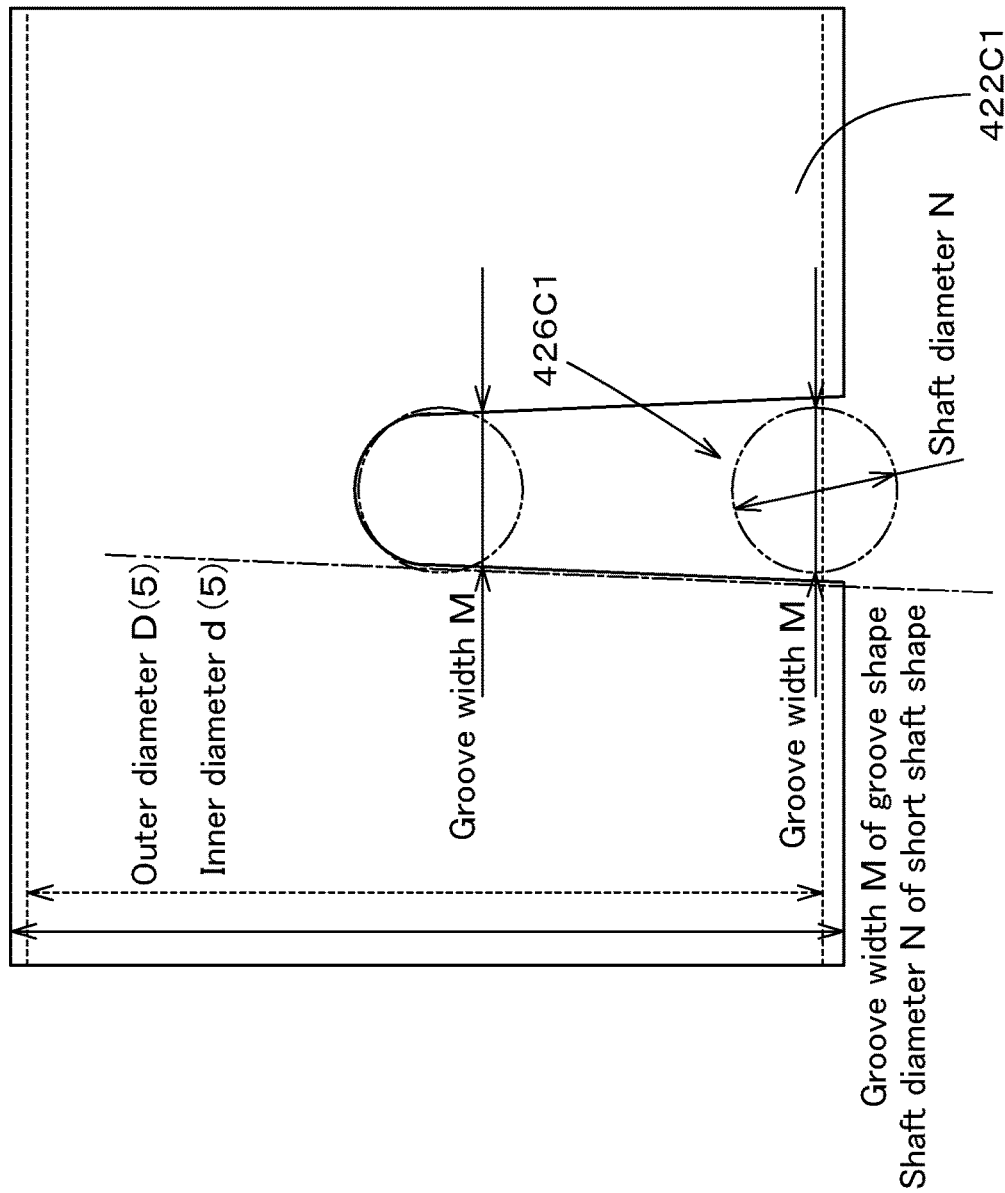
FIG. 13I is a partial view (8) of FIG. 13A.
Figure 13J:
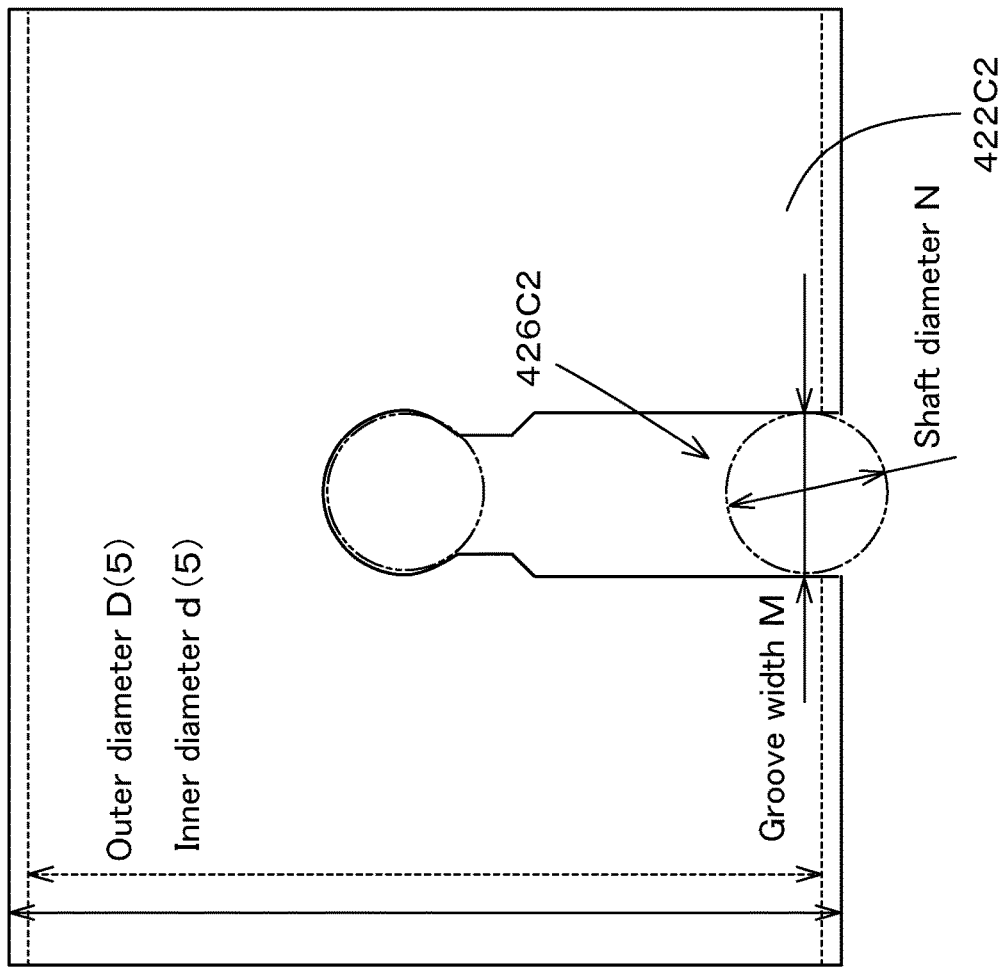
FIG. 13J is a partial view (9) of FIG. 13A.

More specifically, the groove shape (lock groove 426) along the circumferential direction may have an area which allows the shaft (lock pin 416) to be more tightly engaged with decreasing distance to the innermost end of the groove along the circumferential direction as illustrated in FIG. 13I, may have an area which has a narrow groove width to allow the shaft (lock pin 416) to be tightly engaged and which is provided near the innermost end of the groove along the circumferential direction as illustrated in FIG. 13J, and may have, near the innermost end of the groove along the circumferential direction, at least one bend at which the groove shape bends from the circumferential direction to another direction other than the circumferential direction as illustrated in FIG. 13G or 13H. The hole closing material 100 is configured such that, since the groove shape (lock groove 426) along the circumferential direction is formed as described above, the external thread 514 and the internal thread 424 can be unscrewed from each other while the proximal connecting part 412 and the distal connecting part 422 remain united and locked.

Moreover, the hole closing material 100 is configured to achieve the following, details of which will be described later in [Usage Embodiments]. While the hole closing material 100 in which the distal end of the delivery cable 500 is connected to the second end 122 by the distal connecting part 422 is entirely contained in the catheter 300, the delivery cable 500 is manipulated, and the second tubular portion 120 is allowed to move out of the catheter 300 through the distal end of the catheter 300 and then the first tubular portion 110 is allowed to move out of the catheter 300 through the distal end of the catheter 300 such that the hole closing material 100 advances in the direction toward the opening of the catheter 300, so that the first end 112 and the second end 122 come close to each other with the substantially middle portion 130 therebetween. The delivery cable 500 is further manipulated and the proximal connecting part 412 and the distal connecting part 422 are united as described earlier and locked so that the proximal connecting part 412 and the distal connecting part 422 remain united, thereby maintaining a state in which the other portions have a tube diameter increased to a size corresponding to the hole to be closed with the hole closing material 100. The delivery cable 500 is further manipulated, the distal connecting part 422 and the distal end of the delivery cable 500 are brought from the connected state into the disconnected state, and the catheter 300, together with the delivery cable 500 inserted in the catheter 300, is separated from the site where there is the hole.

Figure 2B:
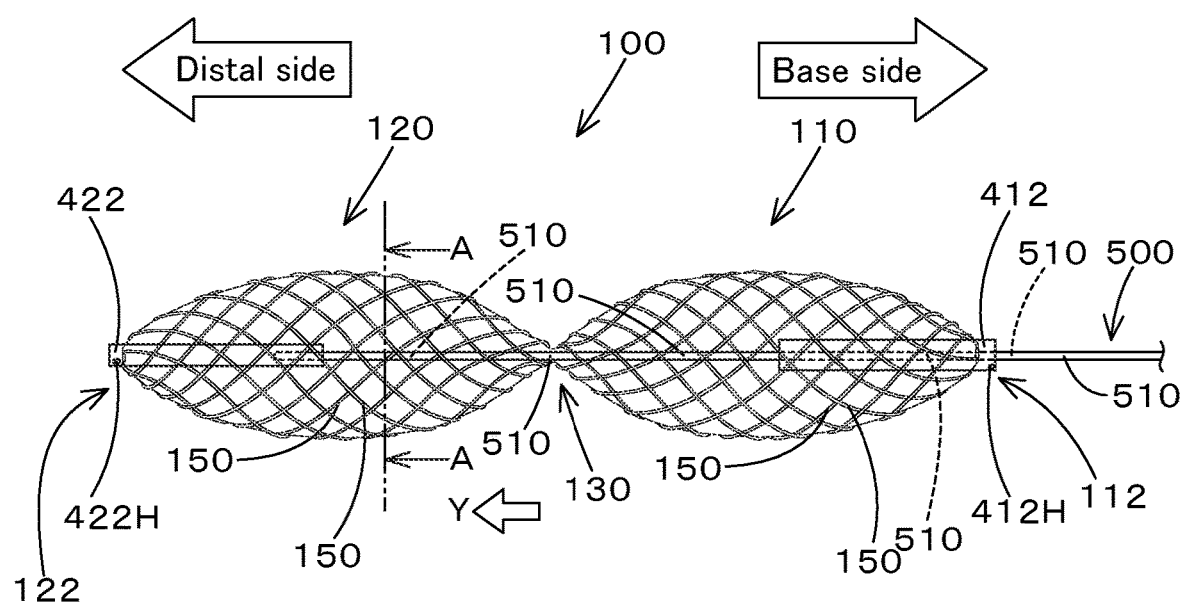
FIG. 2B is an overall view of the hole closing material 100 illustrated in FIG. 1B (the distance between the first end and the second end is in an intermediate state).
Figure 5C:
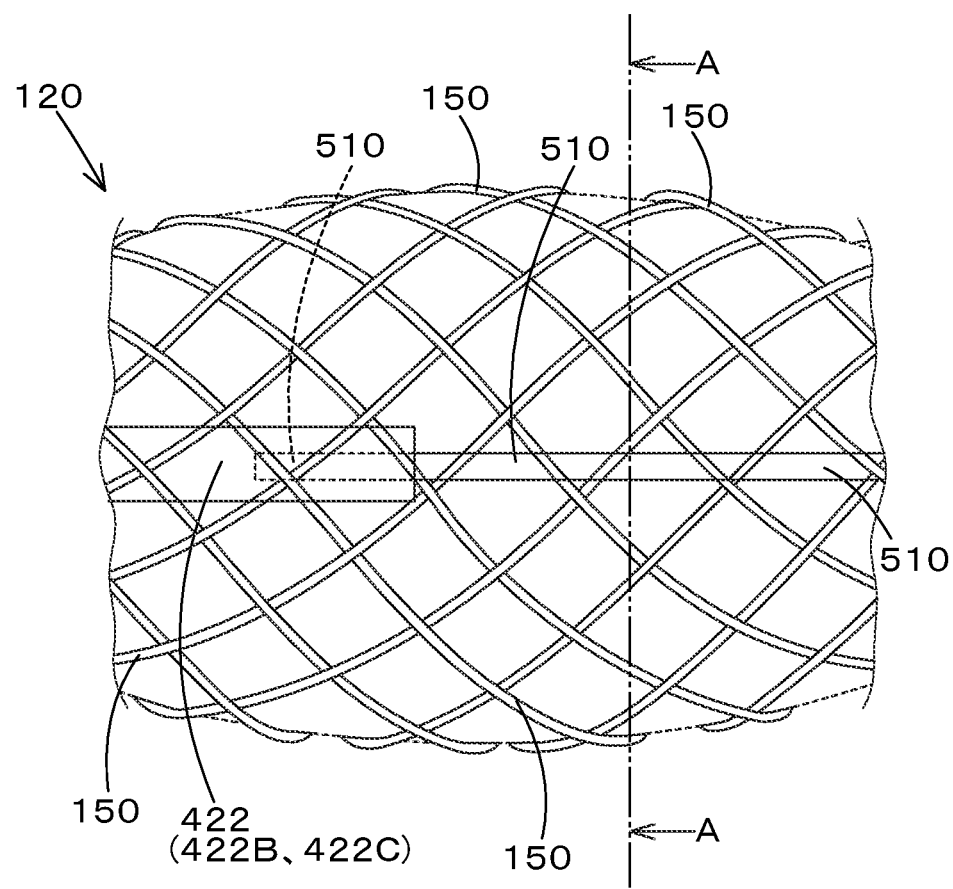
FIG. 5C is a partial side view of the hole closing material 100 in the state shown in FIG. 2B.
Figure 5D:
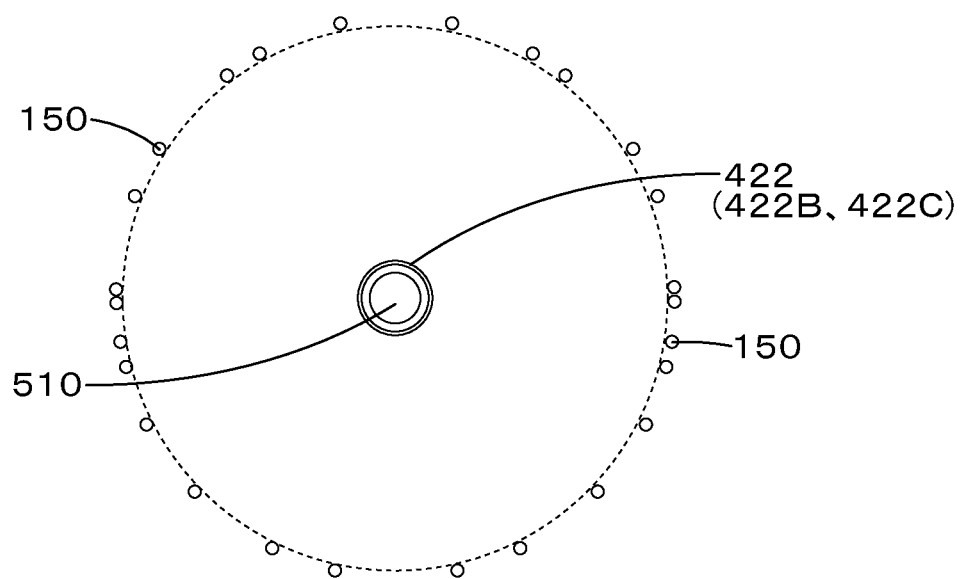
FIG. 5D is a cross-sectional view taken along A-A in FIG. 5C.

FIG. 5C is a partial side view of the hole closing material 100 illustrated in FIGS. 1B, 2B, 3B, and 4B, and FIG. 5D is a cross-sectional view taken along A-A in FIGS. 2B and 5C. Note that although FIG. 5D is a cross-sectional view of the hole closing material 100 (more specifically, the second tubular portion 120), FIG. 5D illustrates a cross-section of the cable body 510 of the delivery cable 500 and does not illustrate the mesh of the bioabsorbable fiber 150 that is visible from a direction indicated by an arrow A. It is noted here that FIG. 5D illustrates not only the cable body 510 of the delivery cable 500 which is visible from the direction indicated by the arrow A but also the distal connecting part's main body 422B and the lock groove cover 422C of the distal connecting part 422. Note that the distal connecting part 422 is substantially in the shape of a cylindrical column, and is formed of: the distal connecting part's main body 422B having the internal thread 424 which is formed in the side facing the external thread 514 of the delivery cable 500, which is screwed onto the external thread 514, and which forms a hollow space; and the lock groove cover 422C which has the lock groove 426 and which covers the distal connecting part's main body 422B. However, a configuration in which the distal connecting part's main body 422B has the lock groove 426 in the outer peripheral surface thereof may be employed, instead of the configuration in which the distal connecting part's main body 422B and the lock groove cover 422C are provided independently of each other (provided as members separate from each other). Furthermore, in FIGS. 1B, 2B, 3B, 4B, 5C, and 5D, the bioabsorbable fiber 150 disposed on the far side of each drawing is not illustrated in order to facilitate the understanding of the presence of the proximal connecting part 412 and the distal connecting part 422 present inside the hole closing material 100, the presence of the cable body 510 of the delivery cable 500, and the mesh of the bioabsorbable fiber 150, and there are some areas in which the external shape of the hole closing material 100 is represented by a dashed line in order to facilitate the understanding of the external shape of the hole closing material 100. Furthermore, there are some areas in which the proximal connecting part 412, the distal connecting part 422, and the cable body 510 of the delivery cable 500 present on the far side of the bioabsorbable fiber 150 in each drawing are represented by solid lines and a part of them overlapping the bioabsorbable fiber 150 is not depicted by dashed lines.

As illustrated in such FIGS. 1 to 5 (particularly FIG. 2), the hole closing material 100 is comprised of two tubular bodies (the first tubular portion 110 and the second tubular portion 120) having a mesh structure formed of a bioabsorbable material, and has a shape which is composed of such two tubular bodies and which is called, for example, a sandglass shape, a figure-of-eight shape, a double spindle shape (shape composed of two continuous long rod-like spindle-shaped objects each of which is thick in the middle and thin at both ends), or a peanut shape (outer shape of a peanut shell containing two nuts). The hole closing material 100 having such a shape has a shape in which the substantially middle portion 130 of the tubular body is narrowed such that the substantially middle portion 130 is smaller in tube diameter than other portions. That is, the first tubular portion 110 with the first end 112 and the second tubular portion 120 with the second end 122 are arranged with the substantially middle portion 130 therebetween.

In the hole closing material 100, the first tubular portion 110 and the second tubular portion 120 are integrally knitted or woven such that the substantially middle portion 130 is smaller in tube diameter than other portions and the hole closing material 100 as a whole has a sandglass shape, figure-of-eight shape, double spindle shape, or peanut shape composed of two tubular bodies, although this does not imply limitation.

In such a case, the shape of the whole hole closing material 100 is formed by, with use of a frame (a three-dimensional paper mold) having such a sandglass shape, figure-of-eight shape, double spindle shape, or peanut shape, knitting or weaving the tubular portions from a strand of the bioabsorbable fiber 150 in conformity with the mold. Further, such a hole closing material 100 having a sandglass shape, figure-of-eight shape, double spindle shape, or peanut shape composed of two tubular bodies as a whole may be formed in the following manner: the first tubular portion 110 and the second tubular portion 120 are integrally knitted or woven to make a tubular body having a substantially uniform diameter and then the tubular body is, for example, thermally set to obtain the substantially middle portion 130 which is smaller in tube diameter than other portions and which has a larger tube diameter than the diameter of the cable body 510 of the delivery cable 500, although this does not imply limitation.

Such a shape, which is achieved by knitting, achieves the following changes in shape (temporal changes in shape), details of which will be described later: with regard to the hole closing material 100 which is entirely contained in the catheter 300 (in the space defined by the inner wall 310) illustrated in FIG. 3, the delivery cable 500 having its distal end connected to the distal connecting part 422 at the second end 122 is manipulated (such that the hole closing material 100 advances in the direction toward the opening 320 of the catheter 300) and the second tubular portion 120 is allowed to move out of the catheter 300 through the opening 320 at the distal end of the catheter 300 in the direction indicated by the arrow Y such that the second tubular portion 120 is pulled out of the catheter 300, so that the second tubular portion 120 is released from the space defined by the inner wall 310 of the catheter 300 and the second tubular portion 120 is brought into the state shown in FIG. 4; and the delivery cable 500 is further manipulated (such that the hole closing material 100 (further) advances in the direction toward the opening 320 of the catheter 300) and the first tubular portion 110 is allowed to move out of the catheter 300 through the opening 320 at the distal end of the catheter 300 in the direction indicated by the arrow Y such that the first tubular portion 110 is pulled out of the catheter 300, so that the first tubular portion 110 is also released from the space defined by the inner wall 310 of the catheter 300 after the tubular portion 120 and the first tubular portion 110 (and the second tubular portion 120) is brought into the state shown in FIG. 1.

As illustrated in FIG. 1, when the hole closing material 100 is not contained in the catheter 300 and is isolated in a space, the first end 112 and the second end 122 are close to each other with the substantially middle portion 130 therebetween, and the first tubular portion 110 and the second tubular portion 120, as the other portions other than the substantially middle portion 130, have an increased tube diameter. With regard to the increased tube diameter, it is particularly preferable that the first tubular portion 110 and the second tubular portion 120 (as the other portions other than the substantially middle portion 130) increase in tube diameter to a size corresponding to a hole to be closed with the hole closing material 100.

As illustrated in FIG. 3, when the hole closing material 100 is not isolated in a space but restricted from freely deforming in radial directions because, for example, the hole closing material 100 is contained in the catheter 300, the first end 112 and the second end 122 are away from each other with the substantially middle portion 130 therebetween, and the first tubular portion 110 and the second tubular portion 120, as the other portions, have a reduced tube diameter. With regard to the reduced tube diameter, it is particularly preferable that the first tubular portion 110 and the second tubular portion 120 (the other portions other than the substantially middle portion 300) decrease in tube diameter to a size corresponding to the catheter 300 in which the hole closing material 100 is contained.

Note that the diameter of the cable body 510 of the delivery cable 500 is smaller than the tube diameter of the substantially middle portion 130.

As described above, by housing the hole closing material 100 in, for example, the catheter 300 to restrict the hole closing material 100 from freely deforming in radial directions or by allowing the hole closing material 100 to move out of the catheter 300 such that the hole closing material 100 is pulled out to release the restriction of free deformation of the hole closing material 100 in radial directions, the first end 112 and the second end 122, which are opposite ends of the hole closing material 100 in the longitudinal direction of the tubular body, can be brought away from each other (contained in the catheter 300) or close to each other (pulled out of the catheter 300). When the hole closing material 100 is allowed to move out of the catheter 300 such that the hole closing material 100 is pulled out of the catheter 300 and free deformation in radial directions is not restricted, as illustrated in FIG. 1, the first end 112 and the second end 122 come close to each other and the other portions other than the substantially middle portion 130 (body portion of the first tubular portion 110 and the body portion of the second tubular portion 120) increase in tube diameter. When the hole closing material 100 is contained in the catheter 300 and free deformation in radial directions is restricted, as illustrated in FIG. 3, the first end 112 and the second end 122 move away from each other and the other portions other than the substantially middle portion 130 (body portion of the first tubular portion 110 and the body portion of the second tubular portion 120) decrease in tube diameter.

Further, as illustrated in FIG. 4, when the second tubular portion 120 is pulled out of the catheter 300 in the direction indicated by the arrow Y, the second tubular portion 120, which has had its shape restricted by the inner wall 310 of the catheter 300 (restricted from freely deforming in radial directions), becomes freely changeable in shape, and only the body portion of the second tubular portion 120 increases in tube diameter. Furthermore, when the first tubular portion 110 is pulled out of the catheter 300 in the direction indicated by the arrow Y, the first tubular portion 110, which has had its shape restricted by the inner wall 310 of the catheter 300 (restricted from freely deforming in radial directions), also becomes freely changeable in shape, and the body portion of the first tubular portion 110 also increases in tube diameter.

The first tubular portion 110 and the second tubular portion 120 of the hole closing material 100 are formed of woven fabric (coarse-woven fabric), knitted fabric, braided fabric, or tubular knitted fabric of the bioabsorbable fiber 150, and are entirely composed of a mesh structure. It should be noted here that the mesh structure is not limited to knitted fabric formed by knitting, but includes a network structure composed of a coarse-woven structure like a window net, as described above. That is, the first tubular portion 110 and the second tubular portion 120 may have a structure called "mesh structure" or a structure called "network structure".

As described above, basically the first tubular portion 110 and the second tubular portion 120 are all made of a bioabsorbable material except for the proximal connecting part 412 and the distal connecting part 422 (these may be simply referred to as "connecting parts", in cases where no distinction is necessary) each composed of a metal piece made of metal (e.g., stainless steel or magnesium), and therefore the entire hole closing material 100 except for the connecting parts is bioabsorbable (the delivery cable 500 is not a constituent element of a medical material according to the present invention and does not remain in a living body, and therefore a material therefor is not particularly limited). Furthermore, treatment to close a hole using the hole closing material 100 changing in shape is performed; in this regard, the hole closing material 100 including the connecting parts employs a material, mesh shape, fiber structure, and fiber cross section that do not damage tissue in a living body even when the shape of the hole closing material 100 is thus changed in the living body.

Note that, usually, the connecting parts are made of, for example, a stainless steel or the like and is not bioabsorbable, but the connecting parts may be made of, for example, an alloy based on magnesium (described later) to be bioabsorbable. The use of an alloy not transmitting X rays (electromagnetic waves having a wavelength of about 1 μm to 10 nm) for the connecting parts is advantageous in that the connecting parts are observable in X-ray imaging, and the use of a bioabsorbable alloy is advantageous in that a metallic member does not remain in the body throughout the whole life and therefore an issue of possible problems in the late post-treatment period does not arise.

The bioabsorbable fiber 150 forming the first tubular portion 110 and the second tubular portion 120 is, for example, at least one type selected from polyglycolic acid, polylactides (poly-D-lactide, poly-L-lactide, and poly-DL-lactide), polycaprolactone, glycolic acid-lactide (D-lactide, L-lactide, or DL-lactide) copolymers, glycolic acid-ε-caprolactone copolymers, lactide (D-lactide, L-lactide, or DL-lactide)-ε-caprolactone copolymers, poly(p-dioxanone), glycolic acid-lactide (D-lactide, L-lactide, or DL-lactide)-ε-caprolactone copolymers, and the like. The at least one type of material is used after being processed into any one of the following forms: monofilament yarn, multifilament yarn, twisted yarn, braid, and the like, and is preferably used in the form of a monofilament yarn.

The material for the bioabsorbable fiber 150 may be a bioabsorbable alloy. Examples of such a bioabsorbable alloy include alloys based on magnesium as a raw material.

The bioabsorbable fiber 150 has a diameter of about 0.001 mm to 1.5 mm, and fiber diameter and type that are suitable for catheterization in which the hole closing material 110 is used are selected. Furthermore, the bioabsorbable fiber 150 may have any of the following cross sections: a circle, an ellipse, and other different shapes (such as a star shape), provided that the in vivo tissue is not damaged. Further, the surface of the bioabsorbable fiber 150 may be treated to have hydrophilicity by plasma discharge, electron beam treatment, corona discharge, ultraviolet irradiation, ozone treatment, or the like. The bioabsorbable fiber 150 may have applied thereon or may be impregnated with a radiopaque material (such as barium sulfate, gold chip, or platinum chip), may be treated to have attached thereon an agent (for example, an agent suitable for catheterization for atrial septal defect), and may be coated with a natural polymer such as collagen and/or gelatin or with a synthetic polymer such as polyvinyl alcohol and/or polyethylene glycol.

The first tubular portion 110 and the second tubular portion 120 are formed in the following manner: the bioabsorbable fiber 150 is, for example, braided to form braided fabric using a braiding machine with multiple (for example, 8 or 12) yarn feeders around a silicone rubber tube (not illustrated) having an outer diameter desired as a monofilament yarn or knitted or woven into a tubular mesh structure having a substantially uniform diameter using a circular knitting machine (not illustrated). After the knitting or weaving, as described earlier, the braided fabric or the tubular mesh structure is formed into a sandglass shape, figure-of-eight shape, double spindle shape, or peanut shape composed of two tubular bodies (first tubular portion 110 and second tubular portion 120). The tube diameters of the first tubular portion 110 and the second tubular portion 120 in a small diameter state are smaller than the inner diameter of the catheter 300, and the first tubular portion 110 and the second tubular portion 120 in a large diameter state have a size preferable for catheterization for atrial septal defect. For example, the tube diameters of the first tubular portion 110 and the second tubular portion 120 in the large diameter state are about 5 mm to 80 mm, preferably about 15 mm to 25 mm. Furthermore, the lengths of the first tubular portion 110 and the second tubular portion 120 and the density of the mesh structure of the hole closing material 100 also have a density preferable for catheterization for atrial septal defect. Note that the first tubular portion 110 and the second tubular portion 120 do not need to have equal tube diameters and do not need to have equal lengths, and the tube diameters and lengths may be changed to suit for catheterization for atrial septal defect.

As has been described, the hole closing material 100 according to the present embodiment illustrated in FIGS. 1A, 2A, 3A, 4A, 5A, and 5B and the hole closing material 100 according to the present embodiment illustrated in FIGS. 1B, 2B, 3B, 4B, 5C, and 5D include the following features.

(First feature) The hole closing material 100 has a sandglass shape, figure-of-eight shape, double spindle shape, or peanut shape that is thin in the substantially middle portion 130 and that is comprised of the first tubular portion 110 and the second tubular portion 120.

(Second feature) The hole closing material 100 includes, at the second end 122 (on the same side of the catheter 300 as the distal end of the catheter 300), the distal connecting part 422 configured to have connected thereto the manipulation wire 500 that passes through the hole closing material 100 from the first end 112 via the substantially middle portion 130 toward the second end 122, and is configured to allow the delivery cable 500 to pass out of the hole closing material 100 through the first end 112.

With the first feature and the second feature, with regard to the hole closing material 100 contained in the catheter 300, when the second tubular portion 120 is allowed to move out of the catheter 300, the second tubular portion 120, which has had its shape restricted by the inner wall 310 of the catheter 300, becomes freely changeable in shape, and only the body portion of the second tubular portion 120 increases in tube diameter, and, furthermore, when the first tubular portion 110 is allowed to move out of the catheter 300, the first tubular portion 110, which has had its shape restricted by the inner wall 310 of the catheter 300, also becomes freely changeable in shape, and the body portion of the first tubular portion 110 also increases in tube diameter. It follows that the body portions increase in tube diameter to a size corresponding to a hole to be closed with the hole closing material 100.

The hole closing material 100 illustrated in FIGS. 1B, 2B, 3B, 4B, 5C, and 5D further includes the following features.

(Third feature) The proximal connecting part 412 and the distal connecting part 422 each have a hollow tubular shape, and are configured to be capable of selectively achieving: "locked" in which the proximal connecting part 412 and the distal connecting part 422 remain united; and "unlocked" in which the proximal connecting part 412 and the distal connecting part 422 do not remain united. The inner diameter d(3) of the proximal connecting part 412 is larger than the outer diameter D(2) of the manipulation wire 500 inserted in the catheter 300, and the distal connecting part 422 is configured to be capable of selectively achieving a connected state in which the distal connecting part 422 is connected to the distal end of the delivery cable 500 and a disconnected state in which the distal connecting part 422 is not connected to the distal end of the delivery cable 500. The hole closing material 100 is configured to allow the delivery cable 500, which has the distal end thereof connected to the distal connecting part 422, to pass through the substantially middle portion 130, be inserted into a hollow tube of the proximal connecting part 412, and pass out of the hole closing material 100 in a direction from the second end 122 to the first end 112 (for example, the first end 112 has a hole which allows passage of the cable body 510 of the delivery cable 500). The hole closing material 100 is configured such that, for example, the internal thread 424 is provided in the distal connecting part 422, the delivery cable 500 has, at the distal end thereof, the external thread 514 configured to be screwed into the internal thread 424, the above-described connected state is achieved by screwing these threads, the above-described disconnected state is achieved by unscrewing these threads, and the disconnected state can be achieved by unscrewing the external thread 514 and the internal thread 424 while the proximal connecting part 412 and the distal connecting part 422 remain united and locked as described above.

In particular, the hole closing material 100 according to the present embodiment illustrated in FIGS. 1A, 2A, 3A, 4A, 5A, and 5B and the hole closing material 100 according to the present embodiment illustrated in FIGS. 1B, 2B, 3B, 4B, 5C, and 5D are suitable for catheterization for atrial septal defect in that the hole closing material 100 brings about the following effects.

(First effect) The hole closing material 100 can be set in the catheter 300 by making the tube diameter of the hole closing material 100 smaller than the inner diameter of the catheter 300 by reducing the tube diameters of the first tubular portion 110 and the second tubular portion 120 which are other portions, by allowing the first end 112 and the second end 122 to move away from each other with the substantially middle portion 130 therebetween (by pulling the first end 112 and the second end 122 in opposite directions such that the first end 112 and the second end 122 move away from each other).

(Second effect) Since the distal connecting part 422 is provided at the second end 122 and the distal end of the delivery cable 500 is connected to the distal connecting part 422, the second tubular portion 120 and the first tubular portion 110 are not allowed to move out of the catheter 300 such that they are pushed out of the catheter 300 but are allowed to move out of the catheter 300 such that they are pulled. This eliminates or reduces the likelihood that, if the second tubular portion 120 and the first tubular portion 110 were pushed out of the catheter 300, the hole closing material 100 would be twisted, and the first end 112 and the second end 122 would not appropriately come close to each other with the substantially middle portion 130 therebetween and the other portions would not appropriately increase in tube diameter to a size corresponding to the hole to be closed with the hole closing material 100. Pulling the second tubular portion 120 and the first tubular portion 110 prevents or reduces such twisting of the hole closing material 100, making it possible to allow the first end 112 and the second end 122 to appropriately come close to each other with the substantially middle portion 130 therebetween and to allow the other portions to appropriately increase in tube diameter to a size corresponding to the hole to be closed with the hole closing material 100. With this, the first tubular portion 110 located in the right atrium and the second tubular portion 120 located in the left atrium come close to each other with the substantially middle portion 130 therebetween, thereby making it possible to close the hole in the atrial septum.

(Third effect) The materials (excluding the connecting parts in some cases) for the hole closing material 100 are all bioabsorbable, and therefore are eventually absorbed by the living body. This substantially eliminates the likelihood that problems will occur in the late post-treatment period.

Furthermore, the hole closing material 100 illustrated in FIGS. 1B, 2B, 3B, 4B, 5C, and 5D is suitable for catheterization for atrial septal defect in that the hole closing material 100 brings about the following effect.

(Fourth effect) After the second effect is brought about, that is, after the first end 112 and the second end 122 have come close to each other with the substantially middle portion 130 therebetween, the delivery cable 500 is further manipulated, the proximal connecting part 412 and the distal connecting part 422 are united as described earlier and locked so that the proximal connecting part 412 and the distal connecting part 422 remain united, thereby maintaining a state in which the other portions have a tube diameter increased to a size corresponding to the hole to be closed with the hole closing material 100. Then, while the proximal connecting part 412 and the distal connecting part 422 remain united and locked as described above, the delivery cable 500 is manipulated, the distal connecting part 422 and the distal end of the delivery cable 500 are disconnected, and the catheter 300, together with the delivery cable 500 inserted in the catheter 300, can be separated from the site where there is the hole. This makes it possible to reliably maintain the state (the shape of the hole closing material 100) in which the first tubular portion 110 located in the right atrium and the second tubular portion 120 located in the left atrium are close to each other with the substantially middle portion 130 therebetween, thereby making it possible to reliably close the hole in the atrial septum.

The following description discusses, with reference to FIGS. 6 to 9, Usage Embodiments in which the hole closing material 100 according to the present embodiment illustrated in FIGS. 1A, 2A, 3A, 4A, 5A, and 5B and the hole closing material 100 according to the present embodiment illustrated in FIGS. 1B, 2B, 3B, 4B, 5C and 5D are used in catheterization for atrial septal defect.

Usage Embodiments

Figure 6:
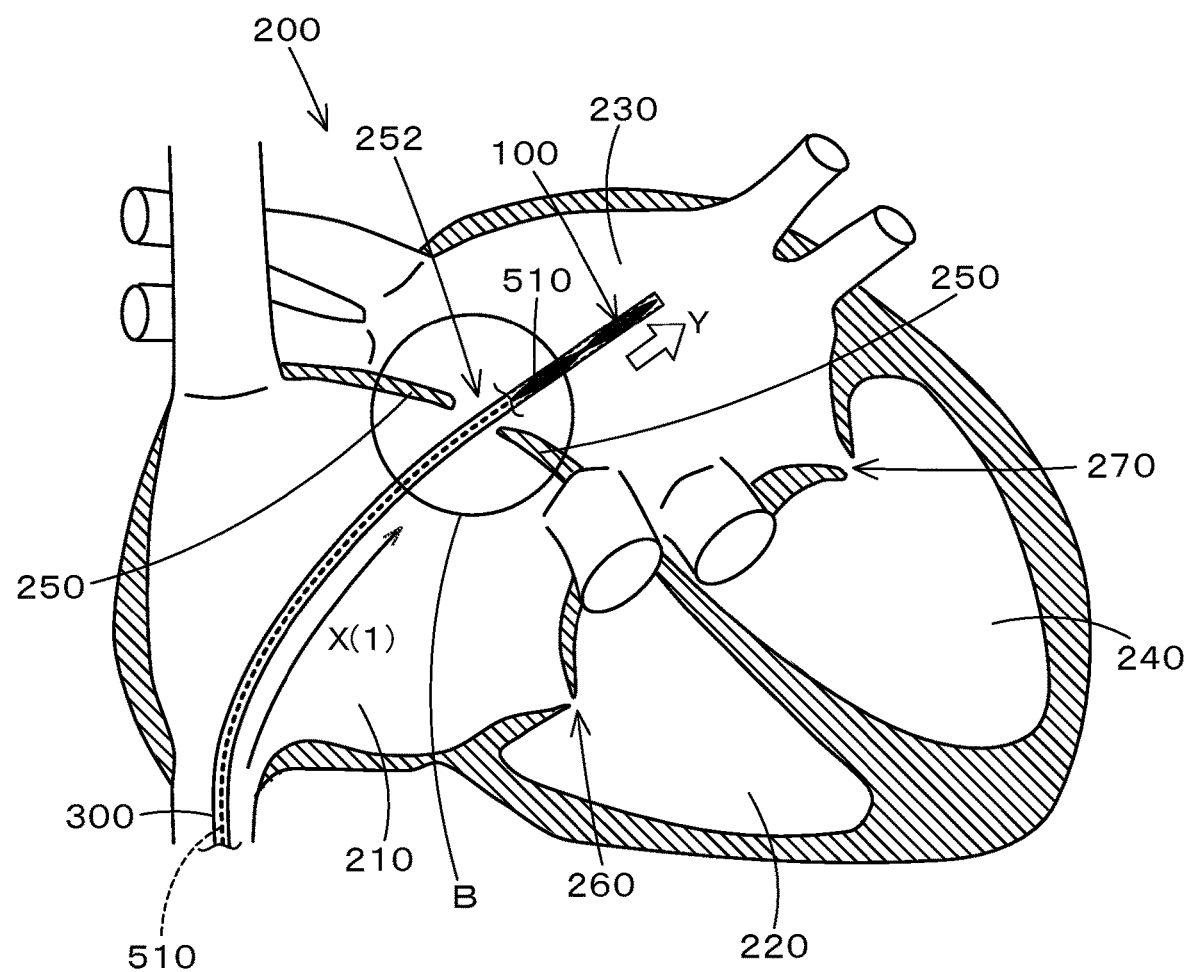
FIG. 6 is a conceptual view in which the hole closing material 100 is used in catheterization for atrial septal defect.
Figure 7A:
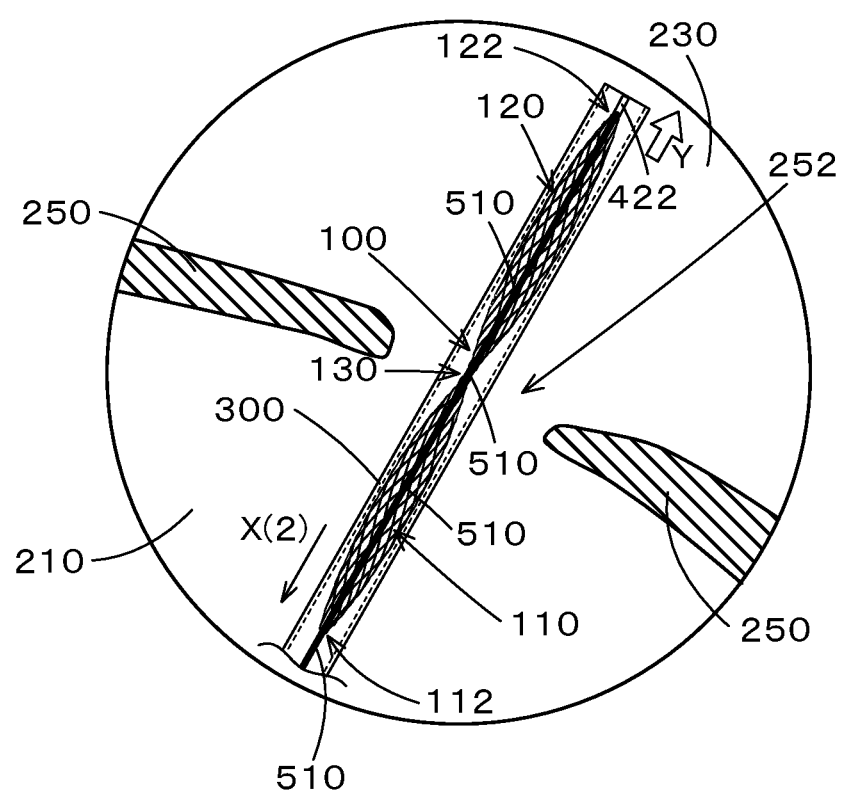
FIG. 7A is an enlarged view (1) of part B in FIG. 6 illustrating a procedure of catheterization using the hole closing material 100 illustrated in FIG. 1A.
Figure 7B:
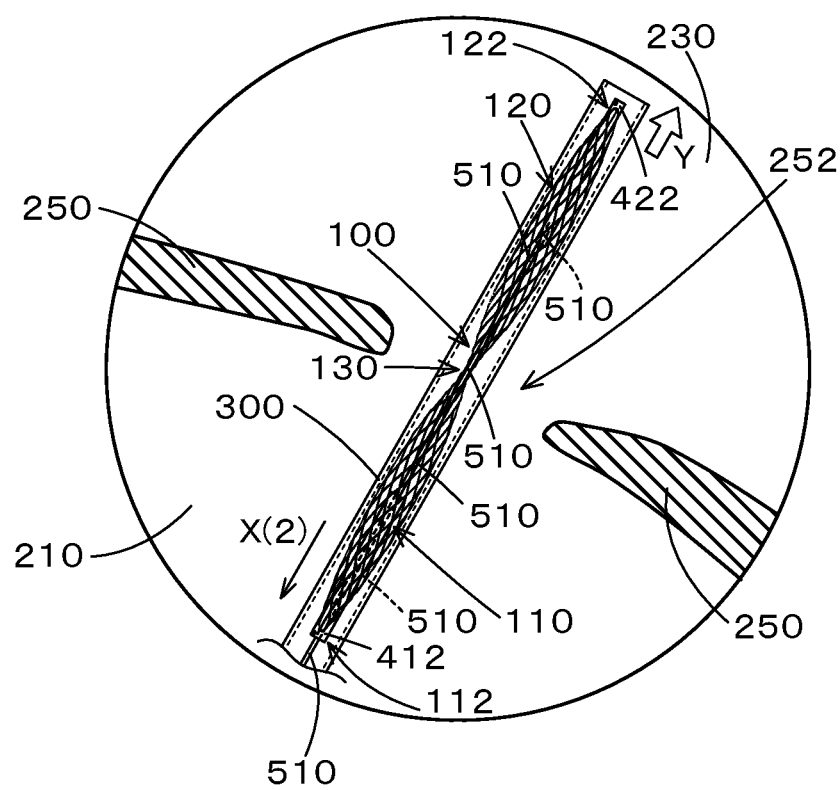
FIG. 7B is an enlarged view (1) of part B in FIG. 6 illustrating a procedure of catheterization using the hole closing material 100 illustrated in FIG. 1B.
Figure 8A:
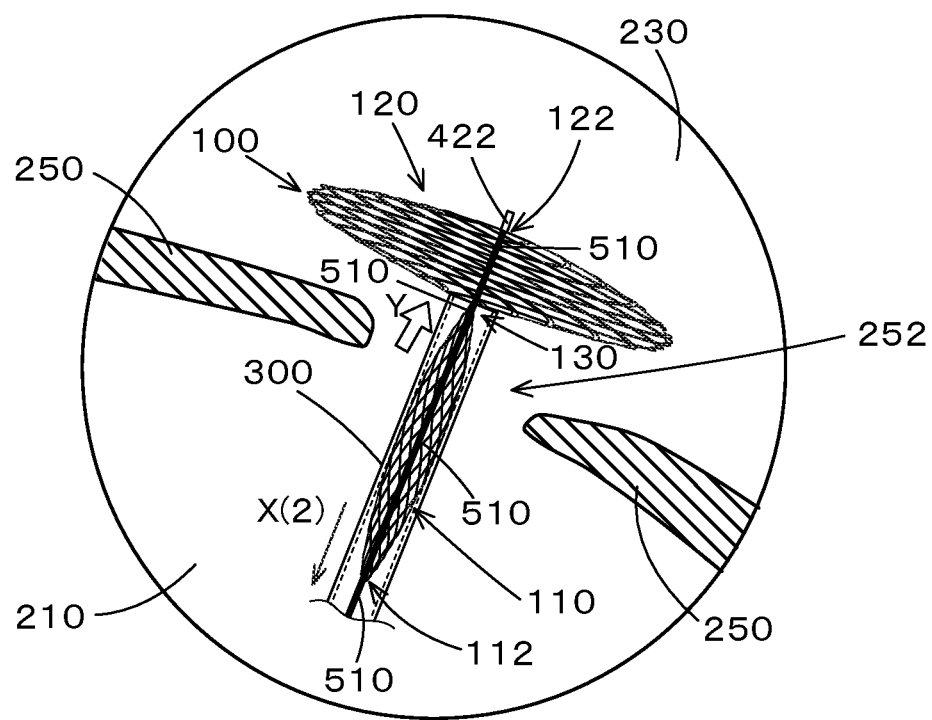
FIG. 8A is an enlarged view (2) of part B in FIG. 6 illustrating the procedure of catheterization using the hole closing material 100 illustrated in FIG. 1A.
Figure 8B:
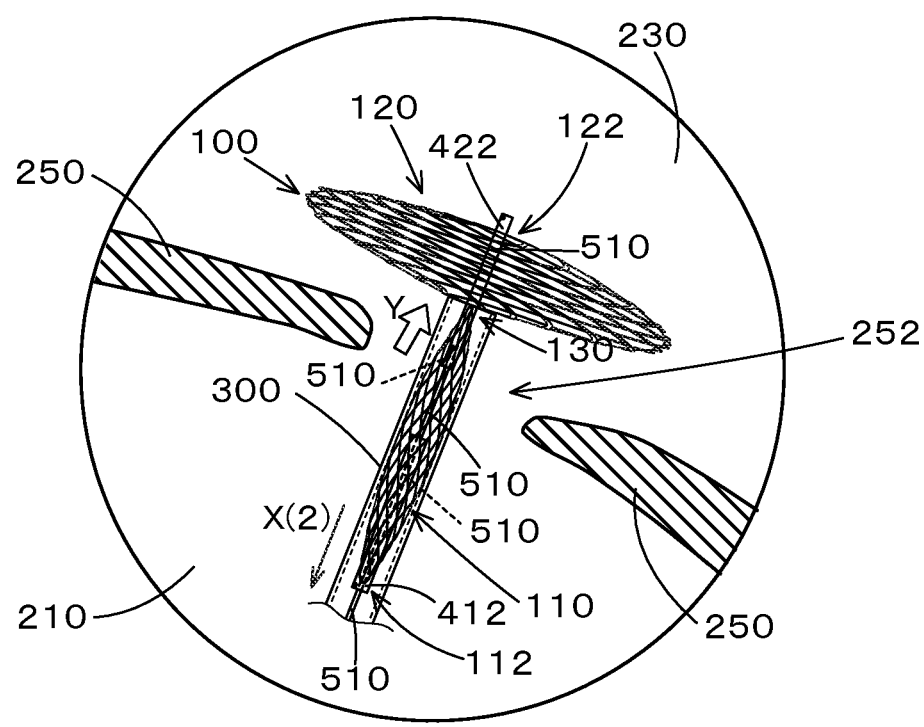
FIG. 8B is an enlarged view (2) of part B in FIG. 6 illustrating the procedure of catheterization using the hole closing material 100 illustrated in FIG. 1B.
Figure 9A:
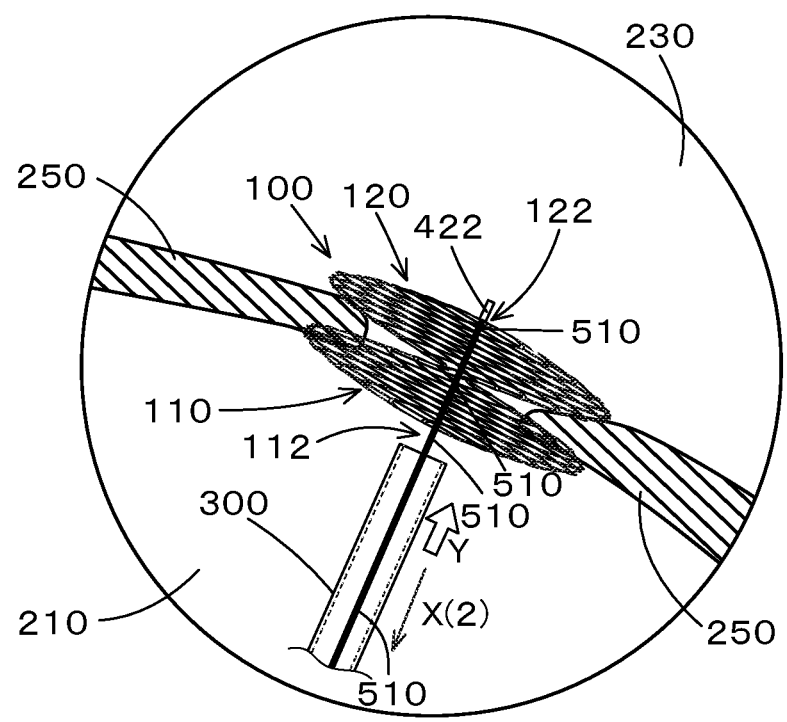
FIG. 9A is an enlarged view (3) of part B in FIG. 6 illustrating the procedure of catheterization using the hole closing material 100 illustrated in FIG. 1A.

FIG. 6 is a conceptual view in which the hole closing material 100 is used in catheterization for atrial septal defect, and FIG. 7 to FIG. 9 are enlarged views of a part B in FIG. 6 and illustrate the procedure of the catheterization. Note that the following description only discusses matters specific to the usage embodiments of the hole closing material 100 according to the present embodiment, and does not specifically discuss general matters because these are the same as those of known catheterization for atrial septal defect.

As illustrated in FIG. 6, a heart 200 of a human has two atria and two ventricles: a right atrium 210 connected to the superior vena cava and the inferior vena cava to receive venous blood from the whole body; a right ventricle 220 connected to the right atrium 210 via a pulmonary artery and a tricuspid valve 260 to send venous blood to the lungs; a left atrium 230 connected to a pulmonary vein to receive arterial blood from the lungs; and a left ventricle 240 connected to the left atrium 230 via the aorta and a mitral valve 270 to send arterial blood to the whole body. Atrial septal defect is a defect in which there is a hole 252 in an atrial septum 250 separating the right atrium 210 and the left atrium 230. Note that, in FIG. 6, an end portion of the catheter 300 (portion on the distal side of the break line) is represented by an imaginary line and thereby the hole closing material 100 contained in the catheter 300 is represented by a solid line for easy understanding.

First, outside the living body, the hole closing material 100, which expands to a size appropriate for the hole 252, is pulled such that the first end 112 and the second end 122 are directed away from each other, thereby causing the hole closing material 100 to have a smaller tube diameter than the inner diameter of the catheter 300, and the hole closing material 100 is set in the catheter 300. The catheter 300 containing the hole closing material 100 is inserted through a femoral vein (see FIG. 3) and the catheter 300 (containing the hole closing material 100) is moved (together with the contained hole closing material 100) in the direction indicated by an arrow X(1) to pass through the hole 252 from the right atrium 210, and the catheter 300 containing the hole closing material 100 is brought close to the left atrium 230 side.

As illustrated in FIG. 6 and FIG. 7, the catheter 300 containing the hole closing material 100 is stopped at a position where the substantially middle portion 130 of the hole closing material 100 substantially corresponds to the hole 252. The delivery cable 500 is manipulated (such that the hole closing material 100 advances in the direction toward the opening 320 of the catheter 300), and, in the living body, because the distal end of the delivery cable 500 is connected to the distal connecting part 422 at the distal end, the second tubular portion 120 is not allowed to move out of the catheter 300 such that the second tubular portion 120 is pushed out of the catheter 300 but is allowed to move out of the catheter 300 in the direction indicated by the arrow Y (in the direction outward of the catheter 300) such that the second tubular portion 120 is pulled. It follows that the second tubular portion 120, which has had its shape (in radial directions) restricted by the inner wall 310 of the catheter 300, becomes freely changeable in shape, and only the body portion of the second tubular portion 120 increases in tube diameter as illustrated in FIG. 8.

Furthermore, the delivery cable 500 is further manipulated (such that the hole closing material 100 (further) advances in the direction toward the opening 320 of the catheter 300) and, in the living body, because the distal end of the delivery cable 500 is connected to the distal connecting part 422 at the distal end, the first tubular portion 110 is not allowed to move out of the catheter 300 such that the tubular portion 110 is pushed out of the catheter 300 but is allowed to move out of the catheter 300 in the direction indicated by the arrow Y (in the direction outward of the catheter 300) such that the tubular portion 110 is pulled after the second tubular portion 120. It follows that the first tubular portion 110, which has had its shape (in radial directions) restricted by the inner wall 310 of the catheter 300, also becomes freely changeable in shape, and only the body portion of the first tubular portion 110 increases in tube diameter as illustrated in FIG. 9.

That is, when the delivery cable 500 is manipulated (such that the hole closing material 100 advances in the direction toward the opening 320 of the catheter 300) at the position where the substantially middle portion 130 of the hole closing material 100 substantially corresponds to the hole 252, the second tubular portion 120 located in the left atrium expands first, and then the first tubular portion 110 located in the right atrium expands. It follows that the first tubular portion 110 located in the right atrium 210 and the second tubular portion 120 located in the left atrium 230 come close to each other with the substantially middle portion 130 (hole 252) therebetween, and that the first tubular portion 110 and the second tubular portion 120 expand. Eventually, as illustrated in FIG. 9, the first tubular portion 110 and the second tubular portion 120 sandwich the atrial septum 250 from both sides, thereby making it possible to close the hole 252 in the atrial septum 250 with the hole closing material 100.

Then, in the body, the cable body 510 is turned (rotated on its axis) so that the external thread 514 turns (rotates on its axis) in the direction opposite to the direction in which the external thread 514 is screwed into the internal thread 424, thereby undoing the screwed connection between the hole closing material 100 and the delivery cable 500. In so doing, the hole closing material 100, which has been placed so as to close the hole 252, does not turn (does not rotate on its axis).

After that, the catheter 300 (which contains the delivery cable 500) is moved in the direction indicated by an arrow X(2) to take the catheter 300 (and the delivery cable 500) out of the living body, thereby completing the treatment. With this, in the living body (technically, in the vicinity of the hole 252), the hole closing material 100 entirely made of a bioabsorbable material (the distal connecting part 422 is excluded in some cases) is placed. As such, since all the materials for the hole closing material 100 placed in the living body are bioabsorbable (the distal connecting part 422 is excluded in some cases), the hole closing material 100 is eventually absorbed by the living body. This substantially eliminates the likelihood that problems will occur in the late post-treatment period.

If the first tubular portion 110 is pushed out of the catheter 300 and then the second tubular portion 120 is pushed out of the catheter 300 in the direction indicated by the arrow Y with the manipulation wire 500 in such a usage embodiment, there may be cases where the hole closing material 100 is twisted, the first end 112 and the second end 122 cannot appropriately come close to each other with the substantially middle portion 130 therebetween, and the other portions do not appropriately increase in tube diameter to a size corresponding to the hole to be closed with the hole closing material 100. However, when the second tubular portion 120 and the first tubular portion 110 are pulled, the twisting of the hole closing material 100 is prevented or reduced, the first end 112 and the second end 122 appropriately come close to each other with the substantially middle portion 130 therebetween, and the other portions can appropriately increase in tube diameter to a size corresponding to the hole to be closed with the hole closing material 100.

As has been described, since the defect hole closing material 100 according to the present embodiment illustrated in FIGS. 1A, 2A, 3A, 4A, 5A, and 5B is entirely made of a bioabsorbable material (connecting part is excluded in some cases) and is eventually absorbed by the living body, there is no or little likelihood that problems will occur in the late posts-treatment period. Furthermore, if the hole closing material 100 is pushed out of the catheter 300, there may be cases where the hole closing material 100 is twisted, the first end 112 and the second end 122 cannot appropriately come close to each other with the substantially middle portion 130 therebetween, and the other portions (first tubular portion 110 and second tubular portion 120) do not appropriately increase in tube diameter to a size corresponding to the hole to be closed with the hole closing material 100; however, when the distal connecting part 422 is provided at the second end 122 and the distal end of the delivery cable 500 is connected to the distal connecting part 422 and the hole closing material 100 is allowed to move out of the catheter 300 such that the hole closing material 100 is pulled, such twisting of the hole closing material 100 is prevented or reduced, the first end 112 and the second end 122 appropriately come close to each other with the substantially middle portion 130 therebetween, and the other portions (first tubular portion 110 and second tubular portion 120) can appropriately increase in tube diameter to a size corresponding to the hole to be closed with the hole closing material 100. It follows that, by merely manipulating the delivery cable 500 such that the hole closing material 100 advances in the direction toward the opening 320 of the catheter 300 at the position of the hole, it is possible to easily change the tube diameter of the hole closing material 100 so that the two tubular bodies (first tubular portion 110 and second tubular portion 120) come close to each other and possible to easily fix that form, making it possible to close the hole 252 in the atrial septum 250.

Figure 9B:
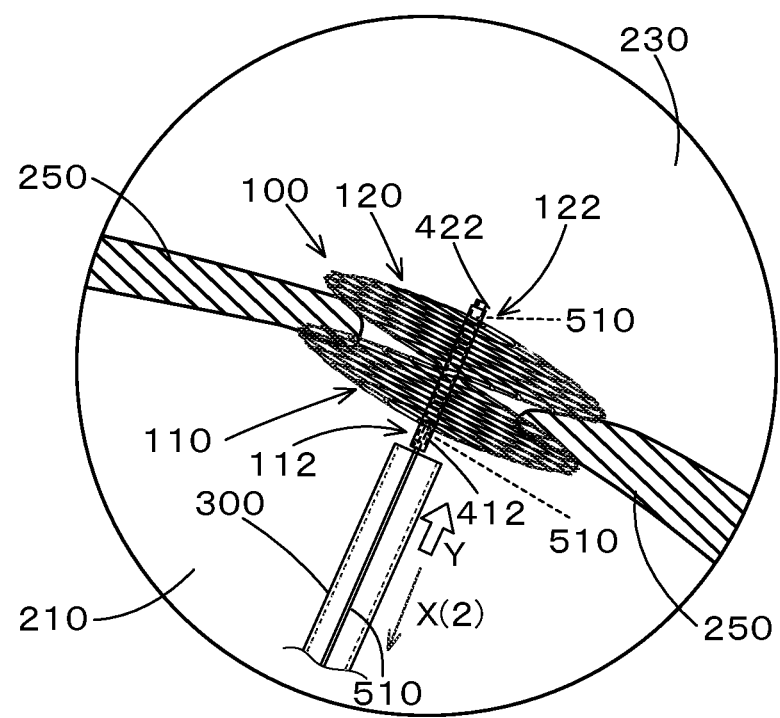
FIG. 9B is an enlarged view (3) of part B in FIG. 6 illustrating the procedure of catheterization using the hole closing material 100 illustrated in FIG. 1B.
Figure 14A:
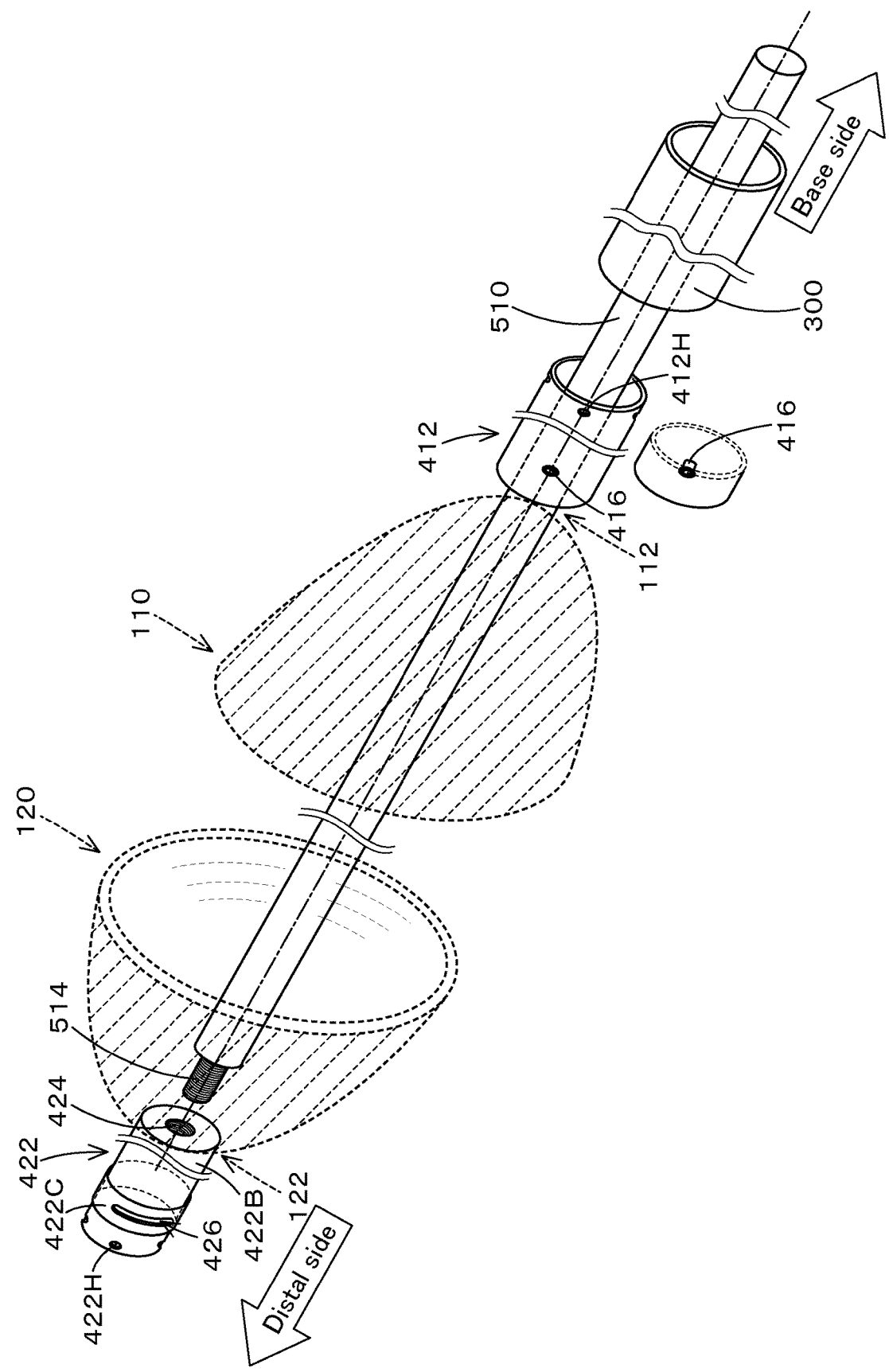
FIG. 14A is a perspective view of FIG. 13A.
Figure 14B:
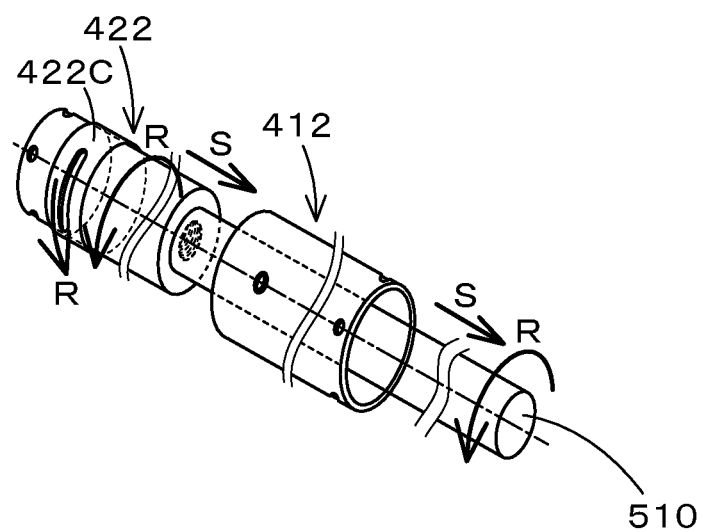
FIG. 14B is a partial view (1) of FIG. 14A.
Figure 14C:
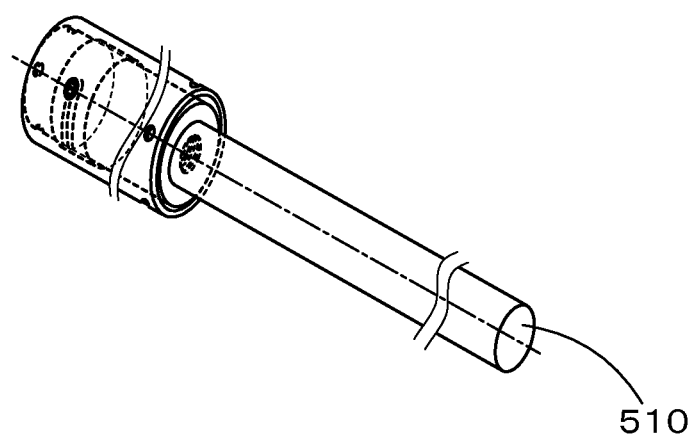
FIG. 14C is a partial view (2) of FIG. 14A.

With regard to the hole closing material 100 illustrated in FIGS. 1B, 2B, 3B, 4B, 5C, and 5D, the state shown in FIG. 9B is the state shown in FIG. 14B (still in unlocked state). A transition from the unlocked state to the state shown in FIG. 14C (locked state) is caused by manipulating the cable body 510 of the delivery cable 500. Note that FIG. 14A serves to facilitate the understanding of the transition from the state shown in FIG. 14B to the state shown in FIG. 14C, and the external thread 514 at the distal end of the delivery cable 500 and the internal thread 424 of the distal connecting part 422 are not screwed together. Furthermore, FIG. 14 corresponds to FIGS. 13A to 13D. FIG. 13A is a side view corresponding to FIG. 14A. FIG. 13B shows a side view, top view, and the opposite side view (from the right leftward in FIG. 13B) of the lock groove cover 422C of the distal connecting part 422 in FIG. 13A. FIG. 13C is an elevational view of the distal connecting part 422 in FIG. 13A as seen in the direction from the proximal end toward the distal end. FIG. 13D is an elevational view of the proximal connecting part 412 in FIG. 13A as seen in the direction from the distal end toward the proximal end. Note that FIGS. 13E to 13J are each a side view of a lock groove cover that is different in groove shape from the lock groove cover 422C, FIG. 13I is an enlarged view of FIG. 13E, and FIG. 13J is an enlarged view of FIG. 13F.

In the unlocked state shown in FIG. 14B, the cable body 510 of the delivery cable 500 is manipulated to move in the direction indicated by an arrow S, thereby inserting the distal connecting part 422, screwed to the cable body 510, into the proximal connecting part 412. In such a case, on the assumption that the catheter 300 has an inner diameter d(1),
the cable body 510 of the delivery cable 500 has an outer diameter D(2),
the proximal connecting part 412 has an inner diameter d(3) and an outer diameter D(3),
the distal connecting part's main body 422B of the distal connecting part 422 has an outer diameter D(4), and
the lock groove cover 422C of the distal connecting part 422 has an inner diameter d(5) and an outer diameter D(5), the following relations hold.

$$d(1) > D(2), D(3), D(4), D(5)$$

$$D(2) < d(3),$$

D(2) is substantially equal to D(4),
D(4) is slightly smaller than or substantially equal to d(5), and
D(5) is slightly smaller than d(3).

As such, since D(4) is slightly smaller than or substantially equal to d(5) and the lock groove cover 422C is a thin sheet metal having a small thickness (which is easy to deform), when the lock groove cover 422C is put on the distal connecting part's main body 422B of the distal connecting part 422, the lock groove cover 422C makes close contact with and is united with the distal connecting part's main body 422B. With this, the lock groove cover 422C does not slide along the longitudinal direction of the cable body 510 of the delivery cable 500 (lateral direction in FIG. 13).

Furthermore, since D(5) is slightly smaller than d(3), the distal connecting part 422 can be inserted into the proximal connecting part 412. In such a case, the lock pin 416 (shaft diameter N) in the shape of a short shaft protrudes inward relative to d(3). The lock pin 416 (shaft diameter N) protrudes inward relative to d(3) so that the lock pin 416 slides on an area defined by the outer diameter D(5) except for the groove portion (lock groove 426) in the lock groove cover 422C until the lock pin 416 is fitted in (engaged with) the lock groove 426 (groove width M) in the shape of a groove. Specifically, in the unlocked state shown in FIG. 14B, when the distal connecting part 422 screwed to the cable body 510 is inserted into the proximal connecting part 412, although the lock pin 416 (shaft diameter N) in the shape of a short shaft protrudes inward relative to d(3), the lock pin 416 slides on an area defined by the outer diameter D(5) except for the groove portion (lock groove 426) in the lock groove cover 422C until the lock pin 416 is fitted in (engaged with) the lock groove 426 (groove width M) in the shape of a groove and, once the lock pin 416 has slid to the lock groove 426 in the shape of a groove, the lock pin 416 is fitted in (engaged with) the lock groove 426 in the shape of a groove.

Under such circumstances, in the unlocked state shown in FIG. 14B, when the cable body 510 of the delivery cable 500 is manipulated such that the cable body 510 is turned (rotated on its axis) in the direction indicated by an arrow R, the lock groove 426 of the lock groove cover 422C rotates and the lock pin 416 engaged with the lock groove 426 advances toward the innermost end of the groove along the circumferential direction. This state means the locked state in which the proximal connecting part 412 and the distal connecting part 422 remain united, which is achieved by setting the shaft diameter N to be slightly smaller than the groove width M. This makes it possible, also when the external thread 514 of the cable body 510 of the delivery cable 500 and the internal thread 424 of the distal connecting part 422 are unscrewed from each other (described later), to unscrew the external thread 514 and the internal thread 424 from each other while keeping the proximal connecting part 41 and the distal connecting part 422 united because of the locked state.

Instead of achieving the locked state by setting the shaft diameter N to be slightly smaller than the groove width M as such, the locked state may be achieved more reliably in the following manner. Note that it is also preferable that the following is employed additionally.

As illustrated in FIG. 13E and FIG. 13I which is an enlarged view thereof, the groove shape (lock groove 426C1) along the circumferential direction may have an area which allows the shaft (lock pin 416) to be more tightly engaged with decreasing distance to the innermost end of the groove along the circumferential direction. Specifically, as illustrated in FIG. 13I, the lock groove 426C1 of a lock groove cover 422C1 is such that the groove width M decreases with decreasing distance to the innermost end of the groove along the circumferential direction. The lock groove cover 422C, which is a thin sheet metal having a small thickness, is less rigid than the lock pin 416 which is made of metal and which is in the shape of a solid shaft; therefore, as the lock pin 416 advances toward the innermost end of the groove along the circumferential direction, the groove width is slightly enlarged by the lock pin 416, making it possible to reliably maintain a state in which the lock pin 416 and the lock groove 426C1 are engaged tightly with each other.

As illustrated in FIG. 13F and FIG. 13J which is an enlarged view thereof, the groove shape (lock groove 426C2) along the circumferential direction may have an area which has a narrow groove width to allow the shaft (lock pin 416) to be tightly engaged and which is provided near the innermost end of the groove along the circumferential direction. Specifically, as illustrated in FIG. 13J, the lock groove 426C2 of a lock groove cover 422C2 has an area in which the groove width M is small, near the innermost end of the groove along the circumferential direction. The lock groove cover 422C, which is a thin sheet metal having a small thickness, is less rigid than the lock pin 416 which is made of metal and which is in the shape of a solid shaft; therefore, only when the lock pin 416 passes through the area where the groove width M is small, the groove width M is slightly enlarged and the lock pin 416 passes through the area where the groove width M is small to reach the innermost end of the lock groove 426C2 along the circumferential direction, making it possible to reliably maintain a state in which the lock pin 416 and the lock groove 426C2 are engaged tightly with each other.

As illustrated in FIG. 13G or 13H, the groove shape (lock groove 426C3 or lock groove 426C4) along the circumferential direction may have, near the innermost end of the groove along the circumferential direction, at least one bend at which the groove shape bends from the circumferential direction to another direction other than the circumferential direction. Specifically, as illustrated in FIG. 13G, the lock groove 426C3 of a lock groove cover 422C3 has, near the innermost end of the groove along the circumferential direction, one bend at which the groove shape bends from the circumferential direction to another direction other than the circumferential direction. As illustrated in FIG. 13H, the lock groove 426C4 of a lock groove cover 422C4 has, near the innermost end of the groove along the circumferential direction, one bend at which the groove shape bends from the circumferential direction to another direction other than the circumferential direction and another bend at which the groove shape bends to the circumferential direction (there are two bends at each of which the groove shape bends from the circumferential direction to another direction other than the circumferential direction and, at the second bend, the groove shape bends to the circumferential direction).

In such a case, it is preferable that the direction to which the groove shape bends at the first bend is opposite to the direction of rotation in which the external thread 514 and the internal thread 424 are unscrewed from each other while the proximal connecting part 412 and the distal connecting part 422 remain united and locked.

Such a configuration, in which the groove shape (lock groove 426C3 or lock groove 426C4) along the circumferential direction has at least one bend at which the groove shape bends from the circumferential direction to another direction other than the circumferential direction, makes it possible to reliably maintain a state in which the lock pin 416 and the lock groove 426C3 or 426C4 are engaged tightly with each other.

As such, by forming a groove shape (lock groove 426, lock groove 426C1, lock groove 426C2, lock groove 426C3, lock groove 426C4, or a combination of any of these) along the circumferential direction, it is possible to unscrew the external thread 514 and the internal thread 424 from each other while the proximal connecting part 412 and the distal connecting part 422 remain united and locked.

Then, in the body, the cable body 510 is turned (rotated on its axis) so that the external thread 514 turns (rotates on its axis) in the direction opposite to the direction in which the external thread 514 is screwed into the internal thread 424, thereby undoing the screwed connection between the hole closing material 100 and the delivery cable 500. In so doing, the hole closing material 100, which has been placed so as to close the hole 252, does not turn (does not rotate on its axis), and the proximal connecting part 412 and the distal connecting part 422 remain united and locked; therefore, as illustrated in FIG. 9B, the first tubular portion 110 and the second tubular portion 120 sandwich the atrial septum 250 from both sides, thereby making it possible to stably and reliably maintain a state in which the hole 252 in the atrial septum 250 is closed with the hole closing material 100.

After that, the catheter 300 (which contains the delivery cable 500) is moved in the direction indicated by the arrow X(2) to take the catheter 300 (and the delivery cable 500) out of the living body, thereby completing the treatment. With this, in the living body (technically, in the vicinity of the hole 252), the hole closing material 100 entirely made of a bioabsorbable material (the connecting parts are excluded in some cases) is placed. As such, since all the materials for the hole closing material 100 placed in the living body are bioabsorbable (the connecting parts are excluded in some cases), the hole closing material 100 is eventually absorbed by the living body. This substantially eliminates the likelihood that problems will occur in the late post-treatment period.

If the first tubular portion 110 is pushed out of the catheter 300 and then the second tubular portion 120 is pushed out of the catheter 300 in the direction indicated by the arrow Y with the manipulation wire 500 in such a usage embodiment, there may be cases where the hole closing material 100 is twisted, the first end 112 and the second end 122 cannot appropriately come close to each other with the substantially middle portion 130 therebetween, and the other portions do not appropriately increase in tube diameter to a size corresponding to the hole to be closed with the hole closing material 100. However, when the second tubular portion 120 and the first tubular portion 110 are pulled, the twisting of the hole closing material 100 is prevented or reduced, the first end 112 and the second end 122 appropriately come close to each other with the substantially middle portion 130 therebetween, and the other portions can appropriately increase in tube diameter to a size corresponding to the hole to be closed with the hole closing material 100.

Furthermore, it is possible to achieve a transition from the unlocked state, in which the proximal connecting part 412 and the distal connecting part 422 are not united, to the locked state, in which the proximal connecting part 412 and the distal connecting part 422 are united; therefore, after the transition to the locked state has been done, the first tubular portion 110 and the second tubular portion 120 sandwich the atrial septum 250 from both sides, thereby making it possible to stably and reliably maintain a state in which the hole 252 in the atrial septum 250 is closed with the hole closing material 100.

As has been described, with the hole closing material 100 according to the present embodiment illustrated in FIGS. 1B, 2B, 3B, 4B, 5C, and 5D, in addition to the hole closing material 100 illustrated in FIGS. 1A, 2A, 3A, 4A, 5A, and 5B, it is possible to achieve a transition from the unlocked state, in which the proximal connecting part 412 and the distal connecting part 422 are not united, to the locked state, in which the proximal connecting part 412 and the distal connecting part 422 are united; therefore, after the transition to the locked state has been done, the first tubular portion 110 and the second tubular portion 120 sandwich the atrial septum 250 from both sides, thereby making it possible to stably and reliably maintain a state in which the hole 252 in the atrial septum 250 is closed with the hole closing material 100. It follows that, by merely manipulating the delivery cable 500 such that the hole closing material 100 advances in the direction toward the opening 320 of the catheter 300 at the position of the hole, it is possible to easily change the tube diameter of the hole closing material 100 so that the two tubular bodies (first tubular portion 110 and second tubular portion 120) come close to each other and possible to easily fix that form, making it possible to stably and reliably maintain a state in which the hole 252 in the atrial septum 250 is closed with the hole closing material 100.

<Variations>

Figure 12A:
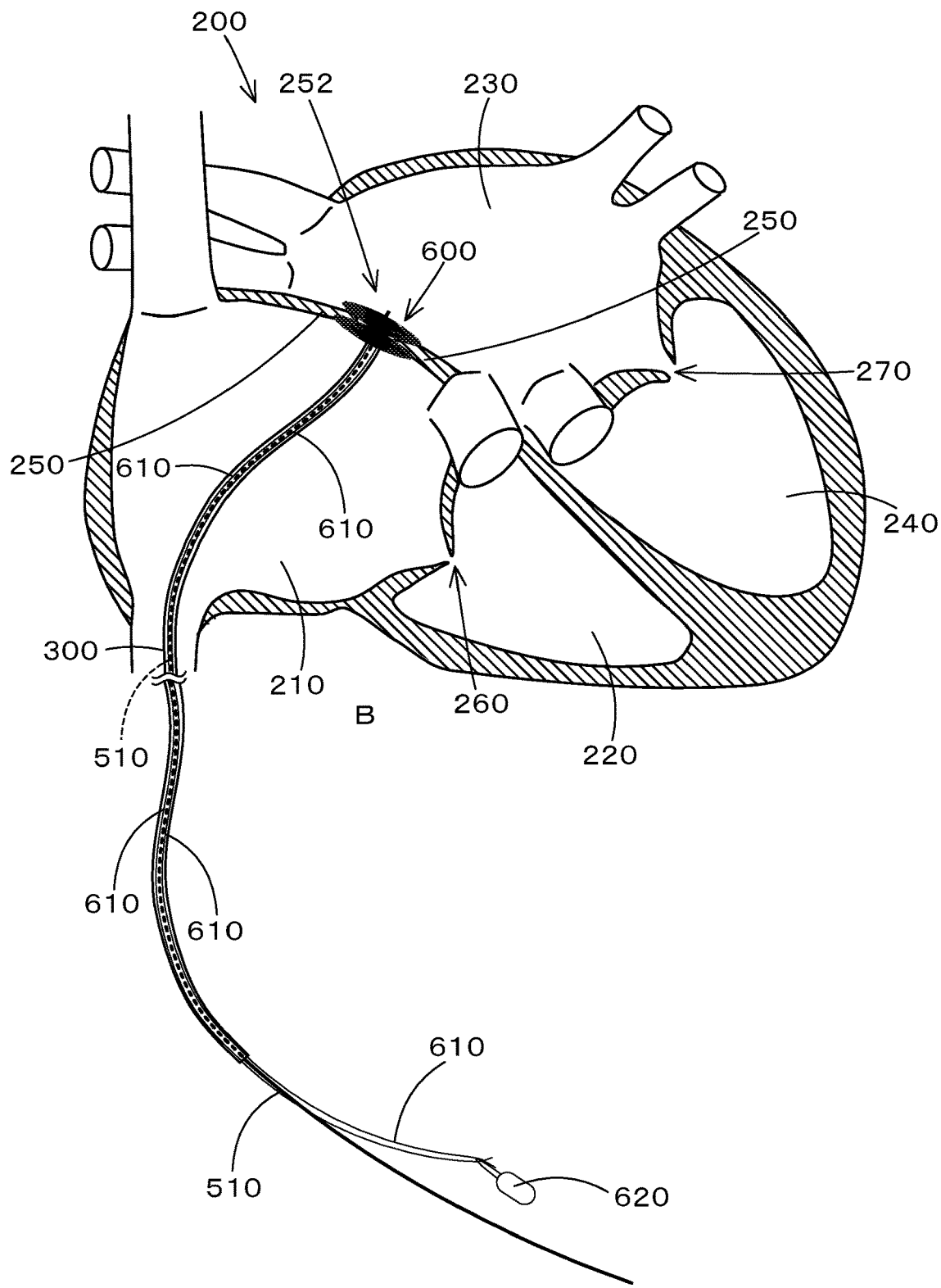
FIG. 12A illustrates a hole closing material 600 which is an example of a medical material according to a variation of the present invention and which has been allowed to move out of the catheter 300 such that the hole closing material 600 is pulled.
Figure 12B:
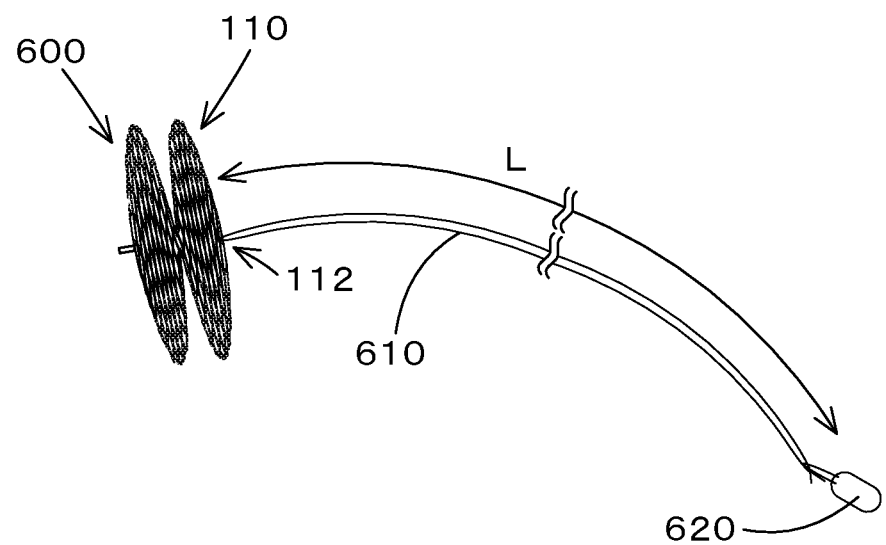
FIG. 12B illustrates the hole closing material 600 which is an example of a medical material according to the variation of the present invention.

The following description discusses, with reference to FIG. 12, a hole closing material 600 according to a variation of the present embodiment, which applies both to the hole closing material 100 illustrated in FIGS. 1A, 2A, 3A, 4A, 5A, and 5B and the hole closing material 100 illustrated in FIGS. 1B, 2B, 3B, 4B, 5C, and 5D. FIG. 12A illustrates the hole closing material 600 according to this variation which has been allowed to move out of the catheter 300 such that the hole closing material 600 is pulled, and FIG. 12B illustrates the hole closing material 600 according to this variation.

The hole closing material 600 has the same configuration as the foregoing hole closing material 100, except that a loop (elongated loop) 610, which is made of the same material as the bioabsorbable fiber 150, is passed through a mesh of the bioabsorbable fiber 150 at the first end 112 (base end) of the first tubular portion 110 and thereby has a loop end thereof connected to the first end of the first tubular portion 110. Therefore, the same configurations are not described here.

The opposite loop end of the loop 610 from the loop end which is passed through a mesh at the first end 112 and is thereby connected to the first end 112, as illustrated in FIG. 12A, passes through the catheter 300 to extend out of the living body and is connected to an anti-falling member 620. Specifically, an overall length L of the loop 610 is greater than the distance from the entrance of the catheter 300 to the exit of the catheter 300. Furthermore, the size of the anti-falling member 620 is larger than the inner diameter of the catheter 300, and the loop 610 is prevented from being drawn into the catheter 300. It is also preferable that the anti-falling member 620 is used as a management tag.

With the hole closing material 600 according to this variation, the loop 610 can be retrieved out of the living body in the following manner: after the hole closing material 600 is placed in the living body as illustrated in FIG. 12A, the loop 610 is cut at any position outside the living body, and one of the cut ends (the end with the anti-falling member 620) is pulled to allow the loop 610 to come out of the mesh. Furthermore, for example, if the hole closing material 600 fell into the heart from the position at which the hole closing material 600 is provided to close the hole 252, it is possible to pull the anti-falling member 620 from the catheter 300 without cutting the loop 610 of the hole closing material 600 and retrieve the hole closing material 600 out of the living body through the catheter 300. As such, since the hole closing material 600 in the living body is connected to the outside of the living body by the loop 610 passed through the catheter 300, it is not necessary to retrieve the hole closing material 600 by performing open chest surgery.

Note that the embodiments disclosed herein should be considered as examples in all aspects and should not be construed as limitations. The scope of the present invention is defined not by the foregoing description but by the claims, and is intended to include all modifications within the scope of the claims and their equivalents.

For example, in the hole closing material 100 illustrated in FIGS. 1B, 2B, 3B, 4B, 5C, and 5D, with regard to the recess (lock groove 426) in the outer peripheral surface of the distal connecting part 422 (more specifically, in the peripheral surface of the lock groove cover 422C of the distal connecting part 422), it is also preferable that a plurality of the recesses are provided at different positions along the longitudinal direction of the delivery cable 500 so that the distance between the first end 112 and the second end 122 of the medical material 100 can be changed. This makes it possible, in the state shown in FIGS. 1B and 9B, to change the length of the substantially middle portion 130 (or the distance between the first end 112 and the second end 122) according to the thickness of the atrial septum which varies among individuals. More specifically, when the thickness of the atrial septum is small, the distal connecting part 422 and the proximal connecting part 412 are locked together on the far side (the distal connecting part 422 is inserted more into the proximal connecting part 412), whereas when the thickness of the atrial septum is large, the distal connecting part 422 and the proximal connecting part 412 are locked together on the near side (the distal connecting part 422 is inserted less into the proximal connecting part 412).

INDUSTRIAL APPLICABILITY

The present invention is suitable for use as a medical material which is set in a catheter to treat a hole in a biological tissue, and is particularly preferable in that the medical material is capable of being released and placed at a treatment site, enables less invasive treatment, is unlikely to cause a problem in the late post-treatment period even when the medical material remains in the body, and is favorably operable.

DESCRIPTION OF THE REFERENCE NUMERAL

100 Medical material (occluder)
110 First tubular portion
112 First end
120 Second tubular portion
122 Second end
130 Substantially middle portion
150 Bioabsorbable fiber
200 Heart
250 Atrial septum
252 Hole
300 Catheter
412 Proximal connecting part
422 Distal connecting part
500 Delivery cable (manipulation wire)

The invention claimed is:
1. A medical material comprised of a tubular body that has a mesh structure formed of a bioabsorbable linear material, wherein:
the medical material has a shape in which a substantially middle portion of the tubular body is smaller in tube diameter than other portions of the tubular body;
the medical material has a first tubular portion with a first end and a second tubular portion with a second end which are arranged with the substantially middle portion therebetween, the first end and the second end being opposite ends in a longitudinal direction of the tubular body;
when the medical material is contained in a catheter such that the first end and the second end are away from each other with the substantially middle portion therebetween and that the other portions have a reduced tube diameter, the second end is located on the same side of the catheter as a distal end of the catheter;
the medical material includes:
a proximal connecting part connected to the mesh structure at the first end; and
a distal connecting part connected to the mesh structure at the second end;
the proximal connecting part and the distal connecting part each have a hollow tubular shape, and are capable of selectively achieving: a locked state in which the proximal connecting part and the distal connecting part remain united; and an unlocked state in which the proximal connecting part and the distal connecting part do not remain united;
an inner diameter of the proximal connecting part is larger than an outer diameter of a delivery cable inserted in the catheter;
the distal connecting part is capable of selectively achieving a connected state in which the distal connecting part is connected to a distal end of the delivery cable and a disconnected state in which the distal connecting part is not connected to the distal end of the delivery cable;
the medical material is configured to allow the delivery cable, which has the distal end thereof connected to the distal connecting part, to pass through the substantially middle portion, be inserted into a hollow tube of the proximal connecting part, and pass out of the medical material in a direction from the second end to the first end,
the proximal connecting part and the distal connecting part each have a hollow cylindrical shape;
an outer diameter of the distal connecting part is smaller than the inner diameter of the proximal connecting part;
the distal connecting part has a recess in an outer peripheral surface thereof;
the proximal connecting part has, on an inner peripheral surface thereof, a protrusion configured to engage with the recess;
the delivery cable is configured such that the delivery cable is rotated in a first direction to allow the recess and the protrusion to engage with each other and, even when the delivery cable is rotated in a second direction opposite to the first direction, the locked state in which the proximal connecting part and the distal connecting part are united is achieved;
the distal connecting part is a hollow tubular object having an internal thread;
the delivery cable has, at the distal end thereof, an external thread configured to be screwed into the internal thread;
the connected state is achieved by screwing the external thread into the internal thread by rotating the delivery cable in the first direction, and the disconnected state is achieved by unscrewing the external thread from the internal thread by rotating the delivery cable in the second direction; and
the medical material is configured such that the external thread and the internal thread are capable of being unscrewed from each other while the proximal connecting part and the distal connecting part remain united and locked.
2. The medical material according to claim 1, wherein:
a shape of the recess in the outer peripheral surface of the distal connecting part has a groove shape provided along a circumferential direction, and a length of the groove shape along the circumferential direction is less than an outer circumference of the distal connecting part;

a shape of the protrusion on the inner peripheral surface of the proximal connecting part is a short shaft shape that extends from the inner peripheral surface toward a cylinder central axis;

a groove width of the groove shape and a shaft diameter of the short shaft shape are substantially equal to each other; and engagement of a shaft portion of the short shaft shape with a groove portion of the groove shape causes the proximal connecting part and the distal connecting part to be united and achieves the locked state.

3. The medical material according to claim 2, wherein the medical material is configured such that the external thread and the internal thread are capable of being unscrewed from each other while the proximal connecting part and the distal connecting part remain united and locked because:

the groove shape along the circumferential direction has an area which allows the shaft to be more tightly engaged with decreasing distance to an innermost end of the groove along the circumferential direction;

the groove shape along the circumferential direction has an area which has a narrow groove width to allow the shaft to be tightly engaged and which is provided near the innermost end of the groove along the circumferential direction; or the groove shape along the circumferential direction has, near the innermost end of the groove along the circumferential direction, at least one bend at which the groove shape bends from the circumferential direction to another direction other than the circumferential direction.

4. The medical material according to claim 1, wherein:

an outer diameter of the distal connecting part is smaller than the inner diameter of the proximal connecting part;

the distal connecting part has a recess in an outer peripheral surface thereof;

the proximal connecting part has, on an inner peripheral surface thereof, a protrusion configured to engage with the recess; and engagement between the recess and the protrusion causes the proximal connecting part and the distal connecting part to be united and achieves the locked state.

5. The medical material according to claim 4, wherein:

a shape of the recess in the outer peripheral surface of the distal connecting part has a groove shape provided along a circumferential direction, and a length of the groove shape along the circumferential direction is less than an outer circumference of the distal connecting part;

a shape of the protrusion on the inner peripheral surface of the proximal connecting part is a short shaft shape that extends from the inner peripheral surface toward a cylinder central axis;

a groove width of the groove shape and a shaft diameter of the short shaft shape are substantially equal to each other; and engagement of a shaft portion of the short shaft shape with a groove portion of the groove shape causes the proximal connecting part and the distal connecting part to be united and achieves the locked state.

6. The medical material according to claim 5, wherein the medical material is configured such that the external thread and the internal thread are capable of being unscrewed from each other while the proximal connecting part and the distal connecting part remain united and locked because:

the groove shape along the circumferential direction has an area which allows the shaft to be more tightly engaged with decreasing distance to an innermost end of the groove along the circumferential direction;

the groove shape along the circumferential direction has an area which has a narrow groove width to allow the shaft to be tightly engaged and which is provided near the innermost end of the groove along the circumferential direction; or the groove shape along the circumferential direction has, near the innermost end of the groove along the circumferential direction, at least one bend at which the groove shape bends from the circumferential direction to another direction other than the circumferential direction.

7. The medical material according to claim 1, wherein the medical material is configured to achieve the following:

while the medical material in which the distal end of the delivery cable is connected to the second end by the distal connecting part is entirely contained in the catheter, the delivery cable is manipulated, and the second tubular portion is allowed to move out of the catheter through the distal end of the catheter and then the first tubular portion is allowed to move out of the catheter through the distal end of the catheter such that the medical material advances in a direction toward an opening of the catheter, so that the first end and the second end come close to each other with the substantially middle portion therebetween;

the delivery cable is manipulated and the proximal connecting part and the distal connecting part are united and the locked state is achieved so that the proximal connecting part and the distal connecting part remain united, thereby maintaining a state in which the other portions have a tube diameter increased to a size corresponding to a hole to be closed with the medical material; and the delivery cable is manipulated, the distal connecting part and the distal end of the delivery cable are disconnected, and the catheter, together with the delivery cable inserted in the catheter, is separated from a site where there is the hole.

* * * * *